(12) United States Patent
Moss et al.

(10) Patent No.: US 7,276,644 B2
(45) Date of Patent: Oct. 2, 2007

(54) TRANSGENIC MOUSE COMPRISING A MYOSIN HEAVY CHAIN ATPASE LOOP 1 MUTATION

(75) Inventors: Richard L. Moss, Middleton, WI (US); Jose A. A. De Santana Pereira, deceased, late of Madison, WI (US); by Bruno Sousa, legal representative, Orlando, FL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/748,354

(22) Filed: Dec. 30, 2003

(65) Prior Publication Data

US 2005/0183147 A1 Aug. 18, 2005

Related U.S. Application Data

(60) Provisional application No. 60/437,073, filed on Dec. 30, 2002.

(51) Int. Cl.
*A01K 67/027* (2006.01)

(52) U.S. Cl. .............................. 800/18; 800/14; 800/3; 800/9

(58) Field of Classification Search .................. 800/18, 800/25, 14, 3, 9; 435/325
See application file for complete search history.

(56) References Cited

OTHER PUBLICATIONS

Kappell et al, Current Opinion in Biotechnology 3:548-553, 1992.*
Hochepied et al, Stem Cells, 2004, 22: 441-447.*
Houdebine, J. Biotechnology, 34: 269-287, 1994.*
Wall, 1996, Theriogenology.*
Cameron, Molecular Biotechnology, 7: 253-265, 1997.*
Sigmund, 2000, Arterioscler. Throm. Vasc. Biol.*
Schoonjans et al, Stem Cells, 2003, 21: 90-97.*
Bauer, C.B. et al. 2000. J. Biol. Chem. 275, 38494-38499.
Bernstein, S.I. et al. 1997. J. Mol. Biol. 271, 1-6.
Dominguez, R. et al. 1998. Cell 94, 559-571.
Fisher, A.J. et al. 1995. Biochemistry 34, 8960-8972.
Geeves, M.A. et al. 1999. Ann. Rev. Biochem. 68, 687-728.
Gulick, A.M. et al. 1997. Bioassays 19, 561-569.
Houdusse, A. et al. 1996. Structure 4, 21-32.
Houdusse, A. et al. 1999. Cell 97, 459-470.
Kambara, T. et al. 1999. J. Biol. Chem. 274, 16400-16406.
Johnson, K.A. et al. 1978. Biochemistry 17, 3432-3442.
Rayment, I. et al. 1993. Science 261, 50-58.
Rovner, A.S. et al. 1997. J. Muscle Res. Cell Motil. 18, 103-110.
Sant'Ana Pereira, J.A.A. et al. 2001. J. Biol. Chem. 276, 4409-4415.
Strang, K. et al. 1994. Circ. Res. 74, 542-549.
Sweeney, H.L. et al. 1998. J. Biol. Chem. 273, 6262-6270.
Schiaffino, S. et al. 1996. Physiol. Rev. 76, 371-423.
Sant'Ana Pereira, J.A.A. et al. 1995. J. Mus. Res. Cell Motil. 16, 21-34.
Alpert, N.R. et al. 1981. Fed Proc 41:192-198.
Anderson, P.A.W. et al. 1991. Circ Res 69:1226-1233.
Berman, M.R. et al. 1988. J Mol Cell Cardiol 20:679-687.
Bonne, G. et al. 1998. Circ Res 83:580-593.
Bottinelli, R. et al. 1994. J Physiol 481:663-675.
Buck, S.H. et al. 1999. Am J Physiol 276:H1167-H1171.
Chen, J. et al. 1998. J Biol Chem 273:1252-1256.
Chizzonite, R.A. et al. 1982. J Biol Chem 257:2056-2065.
Coviello, D.A. et al. 1997. Am J Human Genet 61:A329.
deTombe, P.P. 1998. Cardiovasc Res 37:367-380.
Diffee, G.M. et al. 1996. Biophys J 71:341-350.
Fentzke, R.C. et al. 1999. J Physiol 517:143-157.
Fitzsimons, D.P. et al. 1998. J Physiol 513:171-183.
Geisterfer-Lowrance, A.A.T. et al. 1996. Science 272:731-734.
Gulick, J. et al. 1997. Circ Res 80:655-664.
Homsher, E. et al. 2000. J Physiol 524:233-243.
Huang, X.P. et al. 1999. Circ Res 84:1-8.
Jones, W.K. et al. 1996. J Clin Invest 98:1906-1917.
Kelley, C. et al. 1993. J Biol Chem 268:12848-12854.
Lowey, S. et al. 1993. Nature 365:454-456.
Lyons, G.E. et al. 1990. J Cell Biol 111:2427-2436.
McDonald, K.S. et al. 1998. J Physiol 511:519-531.
Mercadier, J.J. et al. 1981. Circ Res 49:525-532.
Miyata, S. et al. 2000. Circ Res 86:386-390.
Morkin, E. 1993. Circulation 87:1451-1460.
Ng, W.A. et al. 1991. Circ Res 69:1742-1750.
Pawloski-Dahm, C.M. et al. 1998. Circulation 97:1508-1513.
Sant'ana Pereira, J.A.A. et al. 1997. Eur J Physiol 435:151-163.
Siemankowski, R.F. et al. 1985. J Biol Chem 82:658-662.
Sweeney, H.L. et al. 1986. Am J Physiol 251:C431-C434.
Sweeney, H.L. et al. 1988. J Biol Chem 263:9034-9039.
Sweeney, H.L. et al. 1998. J Biol Chem 273:6262-6270.
VanBuren, P. et al. 1995. Circ Res 77:439-444.
VanBuren, P. et al. 1994. Proc. Natl Acad Sci 91:12403-12407.
Wolska, B. et al. 1999. Circ Res 84:745-751.

\* cited by examiner

*Primary Examiner*—Deborah Crouch
*Assistant Examiner*—Magdalene Sgagias
(74) *Attorney, Agent, or Firm*—Quarles & Brady LLP

(57) ABSTRACT

The invention provides a transgenic mouse that is a model for myocardial function. Also provided are methods for using the transgenic mouse model to study heart muscle, cardiac disease and identify compounds effective in treating or preventing cardiac disease.

1 Claim, 9 Drawing Sheets

Fig. 2 Amino acid sequence composition correspondent to the S-1 region of the α-MHC in rat and mouse.

| | |
|---|---|
| Rat α | MTDAQMADFGA-ARYLRKSEKERLEAQTRPFDIRTECFVPDDKEEYVKAKIVSR |
| Mouse α | ............A.Q...................................... |
| | |
| Rat α | EGGKVTAETENGKTVTVKEDQVMQQNPPKFDKIEDMAMLCHTFLHEPAVLYNL |
| Mouse α | .................................................... |
| | |
| Rat α | KERYAAWMIYTYSGLFCVTVNPYKWLPVYNAEVVAAYRGKKRSEAPPHIFSIS |
| Mouse α | .................................................... |
| | |
| Rat α | DNAYQYMLTDRENQSILITGESGAGKTVNTKRVIQYFASIAAIGDRSKKDNPN |
| Mouse α | .................................................... |
| | |
| Rat α | KGTLEDQIIQANPALEAFGNAKTVRNDNSSRFGKFIRIHFGATGKLASADIET |
| Mouse α | .................................................... |
| | |
| Rat α | EKSRVIFQLKAERNYHIFYQILSNKKPELLDMLLVTNNPYDYAFVSQGEVSVA |
| Mouse α | .................................................... |
| | |
| Rat α | SIDDSEELLATDSAFDVLGFTAEEKAGVYKLTGAIMHYGNMKFKQKQREEQAE |
| Mouse α | ..................S................................. |
| | |
| Rat α | PDGTEDADKSAYLMGLNSADLLKGLCHPRVKVGNEYVTKGQSVQQVYYSIGAL |
| Mouse α | .................................................... |
| | |
| Rat α | AKSVYEKMFNWMVTRINATLETKQPRQYFIGVLDIAGFEIFDFNSFEQLCINF |
| Mouse α | .................................................... |
| | |
| Rat α | TNEKLQQFFNHHMFVLEQEEYKKEGIEWEFIDFGMDLQACIDLIEKPMGIMSI |
| Mouse α | .................................................... |
| | |
| Rat α | LEEECMFPKATDMTFKAKLYDNHLGKSNNFQKPRNVKGKQEAHFSLVHYAGTV |
| Mouse α | .................................................... |
| | |
| Rat α | DYNILGWLEKNKDPLNETVVGLYQKSSLKLMATLFSTYASADTGDSGKGKGGK |
| Mouse α | .................................................... |
| | |
| Rat α | KKGSSFQTVSALHRENLNKLMTNLRTTHPHFVRCIIPNERKAPGVMDNPLVMH |
| Mouse α | .................................................... |
| | |
| Rat α | QLRCNGVLEGIRICRKGFPNRILYGDFRQRYRILNPAAIPEGQFIDSGKGAEK |
| Mouse α | ..............................................R..... |
| | |
| Rat α | LLGSLDIDHNQYKFGHTKVFFKAGLLGLLEEMRDERLSRITRIQAQARGQLMR |
| Mouse α | .................................................... |
| | |
| Rat α | IEFKKMVERRDALLVIQWNIRAFMGVKNWPWMK ... |
| Mouse α | ................................. |

Fig. 3 A)
B)
C)
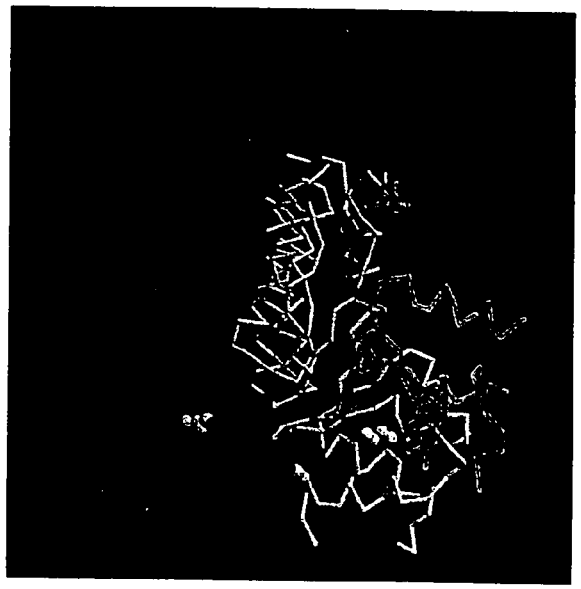

Fig. 4A   Amino acid sequence alignment of the NH2 terminal sub-domain in myosins II.

```
Ch Sk      6   ....EMAAF GEAAPYLRzS EKERIEAQNz PFDAzSSVFV .....VHPKE
Ch Sm      2   AQKPL... .SDDEKFLFV DKNFVNNPLA QADWSAKKLV WV...PSEKH
Dicty      4   ....IHDR TSDYHKYLKV KQG..DSDLF KLTVSDKRYI WYNPDPDERD
Scallop    6     FSD.PDF Q....YLAVD RKKLMKEQTA AFDG..KKNC WV...PDEKE Rat α      1   MTDAQMADF GA.ARYLRKS EKERLEAQTR PFDIRTECFV .....PDDKE
Mouse α □      ·MTDAQMADF GAAAQYLRKS EKERLEAQTR PFDIRTECFV      PDDKE
Human α □
Rat ß      1   MADREMAAF GAGAPFLRKS EKERLEAQTR PFDLKKDVFV .....PDDKE
Human ß    1   MGDSEMAVF GAAAPYLRKS EKERLEAQTR PFDLKKDVFV      PDDKQ
Pig ß
```

Fig. 4B   Amino acid sequence alignment of the converter domain in myosins II.

```
Ch Sk     727  RVLNASAIPE GQFMDSKQAS EKLLGGGDVD HTQYAFGHTz VFFzAGLLGL
Ch Sm     737  EILAANAIPK G.FMDGKQAC ILMIKALELD PNLYRIGQSK IFFRTGVLAH
Dicty     708  YLLAPN.VPR D.AEDSQKAT D.VLKHLNID PEQYRFGITK IFFRAGQLAR
Scallop   721  SILAPNAIPQ G.FVDGKTVS EKILAGLQMD PAEYRLGTTK VFFKAGVLGN Rat α          RILNPAAIPE GQFIDSGKGA EKLLGSLDID HNQYKFGHTK VFFKAGLLGL
Mouse α        RILNPAAIPE GQFIDSRKGA EKLLGSLDID HNQYKFGHTK VFFKAGLLGL
Rat ß          RILNPAAIPE GQFIDSRKGA EKLLGSLDID HNQYKFGHTK VFFKAGLLGL
```

Fig. 4C  Amino acid sequence alignment of the sub-domain comprising the G342S mutation in myosins II.

```
                              #
Ch Sk     340     I L G F S A D E z T
Ch Sm     341     I M G F T E E E Q T
Dicty     234     I V G F S Q E E Q M
Rat α             V L G F T A E E K A
Mouse α           V L S F T A E E K N
Human α.........  V L G F T S E E K N
Rat ß             V L G F T P E E K N
Pig ß             V L G F T S E E K N
Human ß           V L G F T S E E K N
Human Emb         I L G F T P E E K S
Rat Emb           I L G F T P E E K S
Ch Emb            I L G F T P D E K T
Human Per         I L G F T P E E K V
Human IIA
Human IIX
Human IIB
Hamster           V L G F T A E E K A
Drosoph
CeIIA             I M G F E D N E T M
RnCaB             V L G F T P E E K N MaCaB             V L G F T S E E K N
Ai II             I L G F T P E E K S
Dm II             I L G F T K Q E K E
Ch SmII           I M G F S E E E Q L
Oc SmII           I M G F S E E E Q L
Ch nmII           I M G I P D E E Q I
Human nmIIA       I M G I P E E E Q M
Rat nmII          I M G I P D E E Q I
Human nmIIB       I M G F S H E E I L
Xl nmII           I M G F S H E E I L
Dm nmII           I M G M T S E D F N
Sc Myo1(IIA)      I I G F S K D Q I R
```

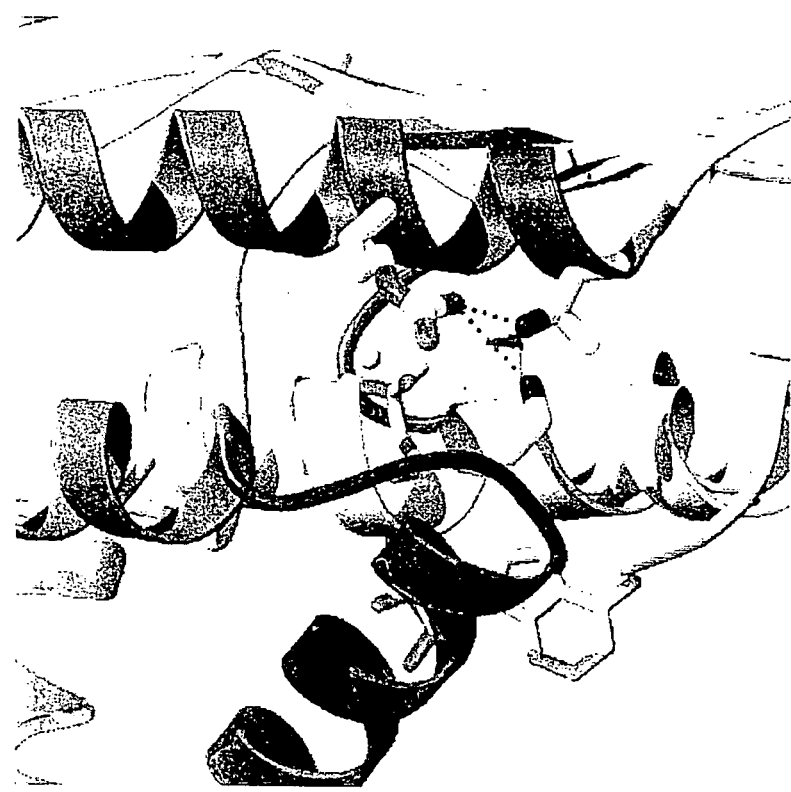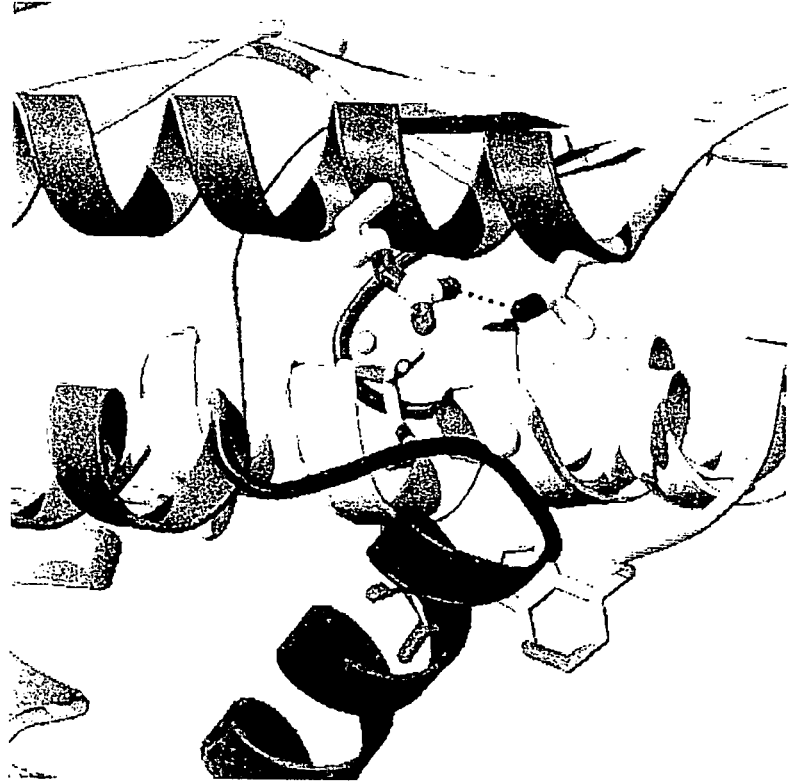
Fig. 6

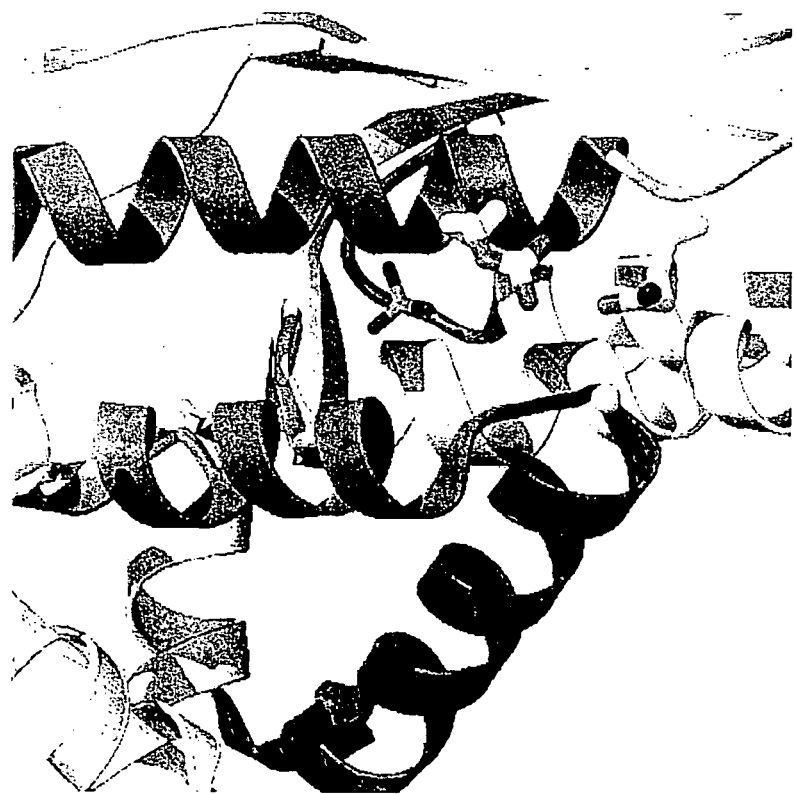
Fig. 7

SEQUENCE LISTING

<160> NUMBER OF SEQ ID NOS: 33

<210> SEQ ID NO 1
<211> LENGTH: 10
<212> TYPE: PRT
<213> ORGANISM: Mus musculus

```
<400> SEQUENCE: 1

Ile Met Gly Phe Thr Glu Glu Glu Gln Thr
1               5                   10

<210> SEQ ID NO 2
<211> LENGTH: 10
<212> TYPE: PRT
<213> ORGANISM: Mus musculus

<400> SEQUENCE: 2

Ile Met Ser Phe Thr Glu Glu Glu Gln Thr
1               5                   10

<210> SEQ ID NO 3
<211> LENGTH: 64
<212> TYPE: DNA
<213> ORGANISM: Mus musculus

<400> SEQUENCE: 3
attgcagcca tagggaccg tagcaagaag gaaaatccta atgcaaacaa gggcaccctg      60
gagg                                                                  64

<210> SEQ ID NO 4
<211> LENGTH: 21
<212> TYPE: PRT
<213> ORGANISM: Mus musculus

<400> SEQUENCE: 4

Ile Ala Ala Ile Gly Asp Arg Ser Lys Lys Glu Asn Pro Asn Ala Asn
1               5                   10                  15

Lys Gly Thr Leu Glu
            20

<210> SEQ ID NO 5
<211> LENGTH: 61
<212> TYPE: DNA
<213> ORGANISM: Sus sp.

<400> SEQUENCE: 5
attgctgcca ttggggaccg cagcaagaag gaccagaccc caggcaaggg caccttggaa      60
g                                                                     61

<210> SEQ ID NO 6
<211> LENGTH: 20
<212> TYPE: PRT
<213> ORGANISM: Sus sp.

<400> SEQUENCE: 6

Ile Ala Ala Ile Gly Asp Arg Ser Lys Lys Asp Gln Thr Pro Gly Lys
1               5                   10                  15

Gly Thr Leu Glu
            20

<210> SEQ ID NO 7
<211> LENGTH: 70
<212> TYPE: DNA
<213> ORGANISM: Mus musculus

<400> SEQUENCE: 7
gcattgcagc cataggcgat cgtagcaaga aggaccagac cccaggcaag gtgagtgtgg      60
gtcataggct                                                            70
```

-continued

<210> SEQ ID NO 8
<211> LENGTH: 17
<212> TYPE: PRT
<213> ORGANISM: Gallus sp.

<400> SEQUENCE: 8

Glu Lys Lys Lys Glu Glu Gln Ser Gly Lys Met Gln Gly Thr Leu Glu
1               5                   10                  15

Asp

<210> SEQ ID NO 9
<211> LENGTH: 18
<212> TYPE: PRT
<213> ORGANISM: Homo sapiens/Sus sp.

<400> SEQUENCE: 9

Glu Lys Lys Lys Glu Glu Pro Thr Ser Gly Lys Met Gln Gly Thr Leu
1               5                   10                  15

Glu Asp

<210> SEQ ID NO 10
<211> LENGTH: 18
<212> TYPE: PRT
<213> ORGANISM: Homo sapiens

<400> SEQUENCE: 10

Glu Lys Lys Lys Glu Glu Val Thr Ser Gly Lys Met Gln Gly Thr Leu
1               5                   10                  15

Glu Asp

<210> SEQ ID NO 11
<211> LENGTH: 18
<212> TYPE: PRT
<213> ORGANISM: Sylvilagus sp.

<400> SEQUENCE: 11

Asp Lys Lys Lys Glu Glu Ala Thr Ser Gly Lys Met Gln Gly Thr Leu
1               5                   10                  15

Glu Asp

<210> SEQ ID NO 12
<211> LENGTH: 18
<212> TYPE: PRT
<213> ORGANISM: Sylvilagus sp.

<400> SEQUENCE: 12

Asp Lys Lys Lys Glu Glu Pro Thr Pro Gly Lys Met Gln Gly Thr Leu
1               5                   10                  15

Glu Asp

<210> SEQ ID NO 13
<211> LENGTH: 17
<212> TYPE: PRT
<213> ORGANISM: Homo sapiens

<400> SEQUENCE: 13

Asp Arg Ser Lys Lys Asp Asn Ala Asn Ala Asn Lys Gly Thr Leu Glu
1               5                   10                  15

Asp

```
<210> SEQ ID NO 14
<211> LENGTH: 17
<212> TYPE: PRT
<213> ORGANISM: Rattus norvegicus

<400> SEQUENCE: 14

Asp Arg Ser Lys Lys Asp Asn Pro Asn Ala Asn Lys Gly Thr Leu Glu
1               5                   10                  15

Asp

<210> SEQ ID NO 15
<211> LENGTH: 17
<212> TYPE: PRT
<213> ORGANISM: Mus musculus

<400> SEQUENCE: 15

Asp Arg Ser Lys Lys Glu Asn Pro Asn Ala Asn Lys Gly Thr Leu Glu
1               5                   10                  15

Asp

<210> SEQ ID NO 16
<211> LENGTH: 16
<212> TYPE: PRT
<213> ORGANISM: Homo sapiens

<400> SEQUENCE: 16

Asp Arg Ser Lys Lys Asp Gln Ser Pro Gly Lys Gly Thr Leu Glu Asp
1               5                   10                  15

<210> SEQ ID NO 17
<211> LENGTH: 16
<212> TYPE: PRT
<213> ORGANISM: Sus sp.

<400> SEQUENCE: 17

Asp Arg Ser Lys Lys Asp Gln Thr Pro Gly Lys Gly Thr Leu Glu Asp
1               5                   10                  15

<210> SEQ ID NO 18
<211> LENGTH: 16
<212> TYPE: PRT
<213> ORGANISM: Rattus norvegicus

<400> SEQUENCE: 18

Asp Arg Ser Lys Lys Asp Gln Thr Pro Gly Lys Gly Thr Leu Glu Asp
1               5                   10                  15

<210> SEQ ID NO 19
<211> LENGTH: 40
<212> TYPE: PRT
<213> ORGANISM: Gallus gallus

<400> SEQUENCE: 19

Ser Glu Gly Glu Ile Thr Val Pro Ser Ile Asp Asp Gln Glu Glu Leu
1               5                   10                  15

Met Ala Thr Asp Ser Ala Ile Asp Ile Leu Gly Phe Ser Ala Asp Glu
            20                  25                  30

Thr Ala Ile Tyr Leu Thr Gly Ala
        35                  40

<210> SEQ ID NO 20
<211> LENGTH: 42
```

```
<212> TYPE: PRT
<213> ORGANISM: Rattus norvegicus

<400> SEQUENCE: 20

Ser Gln Gly Glu Thr Thr Val Ala Ser Ile Asp Asp Ser Glu His
1               5                   10                  15

Met Ala Thr Asp Ser Ala Phe Asp Val Leu Gly Phe Thr Pro Glu Glu
            20                  25                  30

Lys Asn Ser Ile Tyr Lys Leu Thr Gly Ala
        35                  40

<210> SEQ ID NO 21
<211> LENGTH: 40
<212> TYPE: PRT
<213> ORGANISM: Homo sapiens

<400> SEQUENCE: 21

Ser Gln Gly Glu Thr Thr Val Ala Ser Ile Asp Asp Ala Glu Leu
1               5                   10                  15

Met Ala Thr Asp Asn Ala Phe Asp Val Leu Gly Phe Thr Ser Glu Glu
            20                  25                  30

Asn Ser Met Tyr Leu Thr Gly Ala
        35                  40

<210> SEQ ID NO 22
<211> LENGTH: 40
<212> TYPE: PRT
<213> ORGANISM: Sus sp.

<400> SEQUENCE: 22

Ser Gln Gly Glu Thr Thr Val Ala Ser Ile Asp Asp Ala Glu Leu
1               5                   10                  15

Met Ala Thr Asp Asn Ala Phe Asp Val Leu Gly Phe Thr Ser Glu Glu
            20                  25                  30

Asn Ser Met Tyr Leu Thr Gly Ala
        35                  40

<210> SEQ ID NO 23
<211> LENGTH: 40
<212> TYPE: PRT
<213> ORGANISM: Rattus norvegicus

<400> SEQUENCE: 23

Ser Gln Gly Glu Val Ser Val Ala Ser Ile Asp Asp Ser Glu Leu
1               5                   10                  15

Leu Ala Thr Asp Ser Ala Phe Asp Val Leu Gly Phe Thr Ala Glu Glu
            20                  25                  30

Ala Gly Val Tyr Leu Thr Gly Ala
        35                  40

<210> SEQ ID NO 24
<211> LENGTH: 40
<212> TYPE: PRT
<213> ORGANISM: Mus musculus

<400> SEQUENCE: 24

Ser Gln Gly Glu Val Ser Val Ala Ser Ile Asp Asp Ser Glu Leu
1               5                   10                  15

Leu Ala Thr Asp Ser Ala Phe Asp Val Leu Ser Phe Thr Ala Glu Glu
            20                  25                  30
```

Ala Gly Val Tyr Leu Thr Gly Ala
        35                  40

<210> SEQ ID NO 25
<211> LENGTH: 41
<212> TYPE: PRT
<213> ORGANISM: Sylvilagus sp.

<400> SEQUENCE: 25

Ser Glu Gly Glu Ile Thr Val Pro Ser Ile Asp Asp Ser Glu Glu Leu
1               5                   10                  15

Met Ala Thr Asp Ser Ala Ile Asp Ile Leu Gly Phe Thr Ser Asp Glu
            20                  25                  30

Arg Val Ser Ile Tyr Leu Thr Gly Ala
        35                  40

<210> SEQ ID NO 26
<211> LENGTH: 13
<212> TYPE: PRT
<213> ORGANISM: Mus musculus

<400> SEQUENCE: 26

Ala Ser Ile Asp Asp Ser Glu Glu Leu Leu Ala Thr Asp
1               5                   10

<210> SEQ ID NO 27
<211> LENGTH: 13
<212> TYPE: PRT
<213> ORGANISM: Sus sp.

<400> SEQUENCE: 27

Ala Ser Ile Asp Asp Ser Glu Glu Leu Met Ala Thr Asp
1               5                   10

<210> SEQ ID NO 28
<211> LENGTH: 13
<212> TYPE: PRT
<213> ORGANISM: Rattus norvegicus

<400> SEQUENCE: 28

Ala Ser Ile Asp Asp Ser Glu Glu His Met Ala Thr Asp
1               5                   10

<210> SEQ ID NO 29
<211> LENGTH: 16
<212> TYPE: PRT
<213> ORGANISM: Mus musculus

<400> SEQUENCE: 29

Ser Ala Phe Asp Val Leu Ser Phe Thr Ala Glu Glu Lys Ala Gly Val
1               5                   10                  15

<210> SEQ ID NO 30
<211> LENGTH: 16
<212> TYPE: PRT
<213> ORGANISM: Sus sp.

<400> SEQUENCE: 30

Asn Ala Phe Asp Val Leu Gly Phe Thr Ala Glu Glu Lys Asn Gly Val
1               5                   10                  15

<210> SEQ ID NO 31
<211> LENGTH: 16
<212> TYPE: PRT

<213> ORGANISM: Rattus norvegicus

<400> SEQUENCE: 31

Ser Ala Phe Asp Val Leu Gly Phe Thr Pro Glu Glu Lys Ala Ser Ile
1               5                   10                  15

<210> SEQ ID NO 32
<211> LENGTH: 828
<212> TYPE: PRT
<213> ORGANISM: Mus musculus

<400> SEQUENCE: 32

Met Thr Asp Ala Gln Met Ala Asp Phe Gly Ala Ala Arg Tyr Leu Arg
1               5                   10                  15

Lys Ser Glu Lys Glu Arg Leu Glu Ala Gln Thr Arg Pro Phe Asp Ile
            20                  25                  30

Arg Thr Glu Cys Phe Val Pro Asp Asp Lys Glu Glu Tyr Val Lys Ala
        35                  40                  45

Lys Ile Val Ser Arg Glu Gly Gly Lys Val Thr Ala Glu Thr Glu Asn
    50                  55                  60

Gly Lys Thr Val Thr Val Lys Glu Asp Gln Val Met Gln Gln Asn Pro
65                  70                  75                  80

Pro Lys Phe Asp Lys Ile Glu Asp Met Ala Met Leu Cys His Thr Phe
                85                  90                  95

Leu His Glu Pro Ala Val Leu Tyr Asn Leu Lys Glu Arg Tyr Ala Ala
            100                 105                 110

Trp Met Ile Tyr Thr Tyr Ser Gly Leu Phe Cys Val Thr Val Asn Pro
        115                 120                 125

Tyr Lys Trp Leu Pro Val Tyr Asn Ala Glu Val Val Ala Ala Tyr Arg
    130                 135                 140

Gly Lys Lys Arg Ser Glu Ala Pro Pro His Ile Phe Ser Ile Ser Asp
145                 150                 155                 160

Asn Ala Tyr Gln Tyr Met Leu Thr Asp Arg Glu Asn Gln Ser Ile Leu
                165                 170                 175

Ile Thr Gly Glu Ser Gly Ala Gly Lys Thr Val Asn Thr Lys Arg Val
            180                 185                 190

Ile Gln Tyr Phe Ala Ser Ile Ala Ala Ile Gly Asp Arg Ser Lys Lys
        195                 200                 205

Asp Asn Pro Asn Lys Gly Thr Leu Glu Asp Gln Ile Ile Gln Ala Asn
    210                 215                 220

Pro Ala Leu Glu Ala Phe Gly Asn Ala Lys Thr Val Arg Asn Asp Asn
225                 230                 235                 240

Ser Ser Arg Phe Gly Lys Phe Ile Arg Ile His Phe Gly Ala Thr Gly
                245                 250                 255

Lys Leu Ala Ser Ala Asp Ile Glu Thr Glu Lys Ser Arg Val Ile Phe
            260                 265                 270

Gln Leu Lys Ala Glu Arg Asn Tyr His Ile Phe Tyr Gln Ile Leu Ser
        275                 280                 285

Asn Lys Lys Pro Glu Leu Leu Asp Met Leu Leu Val Thr Asn Asn Pro
    290                 295                 300

Tyr Asp Tyr Ala Phe Val Ser Gln Gly Glu Val Ser Val Ala Ser Ile
305                 310                 315                 320

Asp Asp Ser Glu Glu Leu Leu Ala Thr Asp Ser Ala Phe Asp Val Leu
                325                 330                 335

Gly Phe Thr Ala Glu Glu Lys Ala Gly Val Tyr Lys Leu Thr Gly Ala

-continued

```
                340                 345                 350
Ile Met His Tyr Gly Asn Met Lys Phe Lys Gln Lys Gln Arg Glu Glu
            355                 360                 365

Gln Ala Glu Pro Asp Gly Thr Glu Asp Ala Asp Lys Ser Ala Tyr Leu
370                 375                 380

Met Gly Leu Asn Ser Ala Asp Leu Leu Lys Gly Leu Cys His Pro Arg
385                 390                 395                 400

Val Lys Val Gly Asn Glu Tyr Val Thr Lys Gly Gln Ser Val Gln Gln
                405                 410                 415

Val Tyr Tyr Ser Ile Gly Ala Leu Ala Lys Ser Val Tyr Glu Lys Met
            420                 425                 430

Phe Asn Trp Met Val Thr Arg Ile Asn Ala Thr Leu Glu Thr Lys Gln
                435                 440                 445

Pro Arg Gln Tyr Phe Ile Gly Val Leu Asp Ile Ala Gly Phe Glu Ile
            450                 455                 460

Phe Asp Phe Asn Ser Phe Glu Gln Leu Cys Ile Asn Phe Thr Asn Glu
465                 470                 475                 480

Lys Leu Gln Gln Phe Phe Asn His His Met Phe Val Leu Glu Gln Glu
                485                 490                 495

Glu Tyr Lys Lys Glu Gly Ile Glu Trp Glu Phe Ile Asp Phe Gly Met
            500                 505                 510

Asp Leu Gln Ala Cys Ile Asp Leu Ile Glu Lys Pro Met Gly Ile Met
            515                 520                 525

Ser Ile Leu Glu Glu Glu Cys Met Phe Pro Lys Ala Thr Asp Met Thr
            530                 535                 540

Phe Lys Ala Lys Leu Tyr Asp Asn His Leu Gly Lys Ser Asn Asn Phe
545                 550                 555                 560

Gln Lys Pro Arg Asn Val Lys Gly Lys Gln Glu Ala His Phe Ser Leu
                565                 570                 575

Val His Tyr Ala Gly Thr Val Asp Tyr Asn Ile Leu Gly Trp Leu Glu
            580                 585                 590

Lys Asn Lys Asp Pro Leu Asn Glu Thr Val Val Gly Leu Tyr Gln Lys
            595                 600                 605

Ser Ser Leu Lys Leu Met Ala Thr Leu Phe Ser Thr Tyr Ala Ser Ala
            610                 615                 620

Asp Thr Gly Asp Ser Gly Lys Gly Lys Gly Gly Lys Lys Lys Gly Ser
625                 630                 635                 640

Ser Phe Gln Thr Val Ser Ala Leu His Arg Glu Asn Leu Asn Lys Leu
                645                 650                 655

Met Thr Asn Leu Arg Thr Thr His Pro His Phe Val Arg Cys Ile Ile
                660                 665                 670

Pro Asn Glu Arg Lys Ala Pro Gly Val Met Asp Asn Pro Leu Val Met
            675                 680                 685

His Gln Leu Arg Cys Asn Gly Val Leu Glu Gly Ile Arg Ile Cys Arg
            690                 695                 700

Lys Gly Phe Pro Asn Arg Ile Leu Tyr Gly Asp Phe Arg Gln Arg Tyr
705                 710                 715                 720

Arg Ile Leu Asn Pro Ala Ala Ile Pro Glu Gly Gln Phe Ile Asp Ser
                725                 730                 735

Gly Lys Gly Ala Glu Lys Leu Leu Gly Ser Leu Asp Ile Asp His Asn
            740                 745                 750

Gln Tyr Lys Phe Gly His Thr Lys Val Phe Phe Lys Ala Gly Leu Leu
            755                 760                 765
```

-continued

Gly Leu Leu Glu Glu Met Arg Asp Glu Arg Leu Ser Arg Ile Thr Arg
    770                 775                 780

Ile Gln Ala Gln Ala Arg Gly Gln Leu Met Arg Ile Glu Phe Lys Lys
785                 790                 795                 800

Met Val Glu Arg Arg Asp Ala Leu Leu Val Ile Gln Trp Asn Ile Arg
                805                 810                 815

Ala Phe Met Gly Val Lys Asn Trp Pro Trp Met Lys
                820                 825

<210> SEQ ID NO 33
<211> LENGTH: 829
<212> TYPE: PRT
<213> ORGANISM: Mus musculus

<400> SEQUENCE: 33

Met Thr Asp Ala Gln Met Ala Asp Phe Gly Ala Ala Ala Gln Tyr Leu
1               5                   10                  15

Arg Lys Ser Glu Lys Glu Arg Leu Glu Ala Gln Thr Arg Pro Phe Asp
                20                  25                  30

Ile Arg Thr Glu Cys Phe Val Pro Asp Asp Lys Glu Glu Tyr Val Lys
            35                  40                  45

Ala Lys Ile Val Ser Arg Glu Gly Gly Lys Val Thr Ala Glu Thr Glu
        50                  55                  60

Asn Gly Lys Thr Val Thr Val Lys Glu Asp Gln Val Met Gln Gln Asn
65                  70                  75                  80

Pro Pro Lys Phe Asp Lys Ile Glu Asp Met Ala Met Leu Cys His Thr
                85                  90                  95

Phe Leu His Glu Pro Ala Val Leu Tyr Asn Leu Lys Glu Arg Tyr Ala
            100                 105                 110

Ala Trp Met Ile Tyr Thr Tyr Ser Gly Leu Phe Cys Val Thr Val Asn
        115                 120                 125

Pro Tyr Lys Trp Leu Pro Val Tyr Asn Ala Glu Val Val Ala Ala Tyr
    130                 135                 140

Arg Gly Lys Lys Arg Ser Glu Ala Pro Pro His Ile Phe Ser Ile Ser
145                 150                 155                 160

Asp Asn Ala Tyr Gln Tyr Met Leu Thr Asp Arg Glu Asn Gln Ser Ile
                165                 170                 175

Leu Ile Thr Gly Glu Ser Gly Ala Gly Lys Thr Val Asn Thr Lys Arg
            180                 185                 190

Val Ile Gln Tyr Phe Ala Ser Ile Ala Ala Ile Gly Asp Arg Ser Lys
        195                 200                 205

Lys Asp Asn Pro Asn Lys Gly Thr Leu Glu Asp Gln Ile Ile Gln Ala
    210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
                245                 250                 255

Gly Lys Leu Ala Ser Ala Asp Ile Glu Thr Glu Lys Ser Arg Val Ile
            260                 265                 270

Phe Gln Leu Lys Ala Glu Arg Asn Tyr His Ile Phe Tyr Gln Ile Leu
        275                 280                 285

Ser Asn Lys Lys Pro Glu Leu Leu Asp Met Leu Leu Val Thr Asn Asn
    290                 295                 300

Pro Tyr Asp Tyr Ala Phe Val Ser Gln Gly Glu Val Ser Val Ala Ser

-continued

```
            305                 310                 315                 320
Ile Asp Asp Ser Glu Glu Leu Leu Ala Thr Asp Ser Ala Phe Asp Val
                325                 330                 335
Leu Ser Phe Thr Ala Glu Glu Lys Ala Gly Val Tyr Lys Leu Thr Gly
                340                 345                 350
Ala Ile Met His Tyr Gly Asn Met Lys Phe Lys Gln Lys Gln Arg Glu
                355                 360                 365
Glu Gln Ala Glu Pro Asp Gly Thr Glu Asp Ala Asp Lys Ser Ala Tyr
                370                 375                 380
Leu Met Gly Leu Asn Ser Ala Asp Leu Leu Lys Gly Leu Cys His Pro
385                 390                 395                 400
Arg Val Lys Val Gly Asn Glu Tyr Val Thr Lys Gly Gln Ser Val Gln
                405                 410                 415
Gln Val Tyr Tyr Ser Ile Gly Ala Leu Ala Lys Ser Val Tyr Glu Lys
                420                 425                 430
Met Phe Asn Trp Met Val Thr Arg Ile Asn Ala Thr Leu Glu Thr Lys
                435                 440                 445
Gln Pro Arg Gln Tyr Phe Ile Gly Val Leu Asp Ile Ala Gly Phe Glu
                450                 455                 460
Ile Phe Asp Phe Asn Ser Phe Glu Gln Leu Cys Ile Asn Phe Thr Asn
465                 470                 475                 480
Glu Lys Leu Gln Gln Phe Phe Asn His His Met Phe Val Leu Glu Gln
                485                 490                 495
Glu Glu Tyr Lys Lys Glu Gly Ile Glu Trp Glu Phe Ile Asp Phe Gly
                500                 505                 510
Met Asp Leu Gln Ala Cys Ile Asp Leu Ile Glu Lys Pro Met Gly Ile
                515                 520                 525
Met Ser Ile Leu Glu Glu Glu Cys Met Phe Pro Lys Ala Thr Asp Met
                530                 535                 540
Thr Phe Lys Ala Lys Leu Tyr Asp Asn His Leu Gly Lys Ser Asn Asn
545                 550                 555                 560
Phe Gln Lys Pro Arg Asn Val Lys Gly Lys Gln Glu Ala His Phe Ser
                565                 570                 575
Leu Val His Tyr Ala Gly Thr Val Asp Tyr Asn Ile Leu Gly Trp Leu
                580                 585                 590
Glu Lys Asn Lys Asp Pro Leu Asn Glu Thr Val Val Gly Leu Tyr Gln
                595                 600                 605
Lys Ser Ser Leu Lys Leu Met Ala Thr Leu Phe Ser Thr Tyr Ala Ser
                610                 615                 620
Ala Asp Thr Gly Asp Ser Gly Lys Gly Lys Gly Gly Lys Lys Lys Gly
625                 630                 635                 640
Ser Ser Phe Gln Thr Val Ser Ala Leu His Arg Glu Asn Leu Asn Lys
                645                 650                 655
Leu Met Thr Asn Leu Arg Thr Thr His Pro His Phe Val Arg Cys Ile
                660                 665                 670
Ile Pro Asn Glu Arg Lys Ala Pro Gly Val Met Asp Asn Pro Leu Val
                675                 680                 685
Met His Gln Leu Arg Cys Asn Gly Val Leu Glu Gly Ile Arg Ile Cys
                690                 695                 700
Arg Lys Gly Phe Pro Asn Arg Ile Leu Tyr Gly Asp Phe Arg Gln Arg
705                 710                 715                 720
Tyr Arg Ile Leu Asn Pro Ala Ala Ile Pro Glu Gly Gln Phe Ile Asp
                725                 730                 735
```

```
Ser Arg Lys Gly Ala Glu Lys Leu Leu Gly Ser Leu Asp Ile Asp His
            740             745             750

Asn Gln Tyr Lys Phe Gly His Thr Lys Val Phe Phe Lys Ala Gly Leu
            755             760             765

Leu Gly Leu Leu Glu Glu Met Arg Asp Glu Arg Leu Ser Arg Ile Thr
        770             775             780

Arg Ile Gln Ala Gln Ala Arg Gly Gln Leu Met Arg Ile Glu Phe Lys
785             790             795             800

Lys Met Val Glu Arg Arg Asp Ala Leu Leu Val Ile Gln Trp Asn Ile
            805             810             815

Arg Ala Phe Met Gly Val Lys Asn Trp Pro Trp Met Lys
            820             825
```

TRANSGENIC MOUSE COMPRISING A MYOSIN HEAVY CHAIN ATPASE LOOP 1 MUTATION

CROSS-REFERENCE TO RELATED APPLICATION

This application claims the benefit of U.S. Provisional Application No. 60/437,073, filed Dec. 30, 2002, incorporated herein by reference.

STATEMENT AS TO RIGHTS TO INVENTIONS MADE UNDER FEDERALLY SPONSORED RESEARCH AND DEVELOPMENT

This work was supported in part by a grant from the National Institutes of Health—NIH 1 R01 HL63167. The Government of the United States of America may have certain rights in this invention.

FIELD OF THE INVENTION

The present invention relates to a transgenic model of myocardial function. In particular, the invention is directed to a transgenic mouse expressing recombinant cardiac myosin with altered kinetic properties that more closely resemble human cardiac myosin.

BACKGROUND OF THE INVENTION

There is considerable interest in the subunit composition of myosin because of the roles of varied expression in determining contractile properties of myocardium and other muscles. Myosin isoforms can be identified in several ways (reviewed in 54) including separation of the native molecules on non-denaturing gels, identification of distinct species of myosin heavy and light chains by SDS-PAGE and Western blots, and immunoreactivity of fixed thin sections of muscle. Each myosin molecule is comprised of 2 heavy chains (MHC) of about 200 kDa and 4 light chains (MLC) with molecular weights between 16 and 25 kDa (18,69). Previous studies have related mechanical properties to the types of myosin that are present, and while $V_{max}$ is thought to be limited by the rate of dissociation of ADP from A.M.ADP (56), the molecular basis for differences in contractile behaviors of muscles with different MHC isoforms is not yet known. This knowledge is critical to ultimate understanding of the basis for adaptive alterations in muscle function and will contribute to improved understanding of contractile dysfunction in diseases such as congestive heart failure, in which the kinetics of contraction can be considerably slowed compared to normal parameters (13).

SUMMARY OF THE INVENTION

The present invention provides a nonhuman transgenic animal having incorporated into its genome a transgene comprising a nucleic acid coding for a mutant α myosin heavy chain (αMHC) expressed in at least the heart of the transgenic animal. The transgenic animal is preferably a mouse. The mutant αMHC is altered to reduce the rate of its motor activity and therefore the transgenic mouse expressing the transgene has increased work and power generating capabilities and slower heart rate better resembling that of a larger mammal, preferably a human. A transgenic mouse according to the present invention more closely resembles human cardiac parameters and is thusly a useful model of myocardial function. The transgenic mouse may further be used to study molecular and cellular aspects associated with cardiac disease, to identify compounds useful for treating or preventing cardiac disease, and to evaluate the effects of external factors (such as diet and exercise) on cardiac disease.

Other objects, features and advantages of the present invention will become apparent after review of the specification, claims and drawings.

BRIEF DESCRIPTION OF THE DRAWINGS

This application contains at least one drawing executed in color.

FIG. 2—Amino acid sequence composition correspondent to the S-1 region of the α-MHC in rat (SEQ ID NO:32) and mouse (SEQ ID NO:33).

FIG. 3A—Ribbon diagram of the ChSK structure (PDB code:2mys) shown in gray, switch-1 is colored yellow, switch-2 is blue and P-loop is pink. The amino acid residues corresponding to amino acids differing between rat α and mouse-α myosins, represented as cpk, are colored red.

FIG. 3B—Superposition of the backbone Cα trace of NH2-terminal (residues 4-150 in ChSk) region of ChSk (yellow), ChSm (1br1, red), *Dictyostelium* (1mmd, dark blue), *Dictyostelium* (1vom, light blue) and scallop (1b7t, green). A14 and Y16 (ChSk) are represented in ball-and-stick mode in yellow.

FIG. 3C—Substitution R741G in superposed structures representative of three different actin-free states of myosin. The backbone Cα trace of the relay (residues 490-520, ChSK) in the three states is colored beige whereas the converter is colored yellow in the ATP state or state I (ChSk; 2mys), red in the pre-power stroke or state II (ChSm; 1br1 and green in ATP state III (scallop;1b7t). Residue 741 (ChSK) is represented in ball and stick. The figures were prepared using Molscript (Kraulis,1991) and Raster-3D (Merrit 1994, 1997)

FIG. 4 (A-C)—Amino acid sequence alignment of the sub-domains comprising substitutions between rat-α and mouse-α MHCs. The sequences of the two α-MHC isoforms were aligned to a vast number of sequences from myosins II: Alignments (A) NH2-terminal sub-domain; (B) converter domain; (C) α-helical region close to the lip of the binding pocket which comprises the G342S substitution between rat and mouse-α MHCs.

FIG. 6 (A-B)—Close-up of the region comprising G343 (G342, ChSK) in ChSm 3D structure complexed with Mg.ADP.AlF$_4^-$ (PDB 1br1). P-loop is colored pink, switch-1 is orange, switch-2 green and α-helix close to the binding pocket is dark orange. Nucleotide analog is colored beige. A) The Cα atom of G343 is represented as a sphere. B) Shows the G343S mutation, where dashed lines represent plausible H-bond interactions between Oγ atom of S343 and NH2 of R445. A449 is also represented in the structure and corresponds to Q448 in ChSk. Side-chain atoms of the amino acid residues are represented in ball-and-stick, following the atom color code: C-yellow, N-blue and O-red.

FIG. 7 (A-B)—Close-up of the region comprising G342 in the ChSk 3D structure without nucleotide at the active site (PDB code:2mys). P-loop is colored pink, switch-1 is orange, switch-2 green and α-helix close to the binding pocket is dark orange. The $SO_4^{2-}$ ion at the active site is drawn as cpk (O—red. and S—green). A) The Cα atom of G342 is represented as a sphere. B) Shows the G342S mutation. In B, small rearrangements of the side-chain atoms of R444 and Q448 were necessary to optimize polar interactions and to avoid steric repulsion with Oγ from S342, respectively. Dashed lines represent plausible H-bond interactions between Oγ atom of S342 with either the NH2 of R442 or Q448. Side-chain atoms of the amino acid residues are represented in ball-and-stick, following the atom color code: C—yellow, N—blue and O—red.

DETAILED DESCRIPTION OF THE INVENTION

I. The Invention

Figure 1:
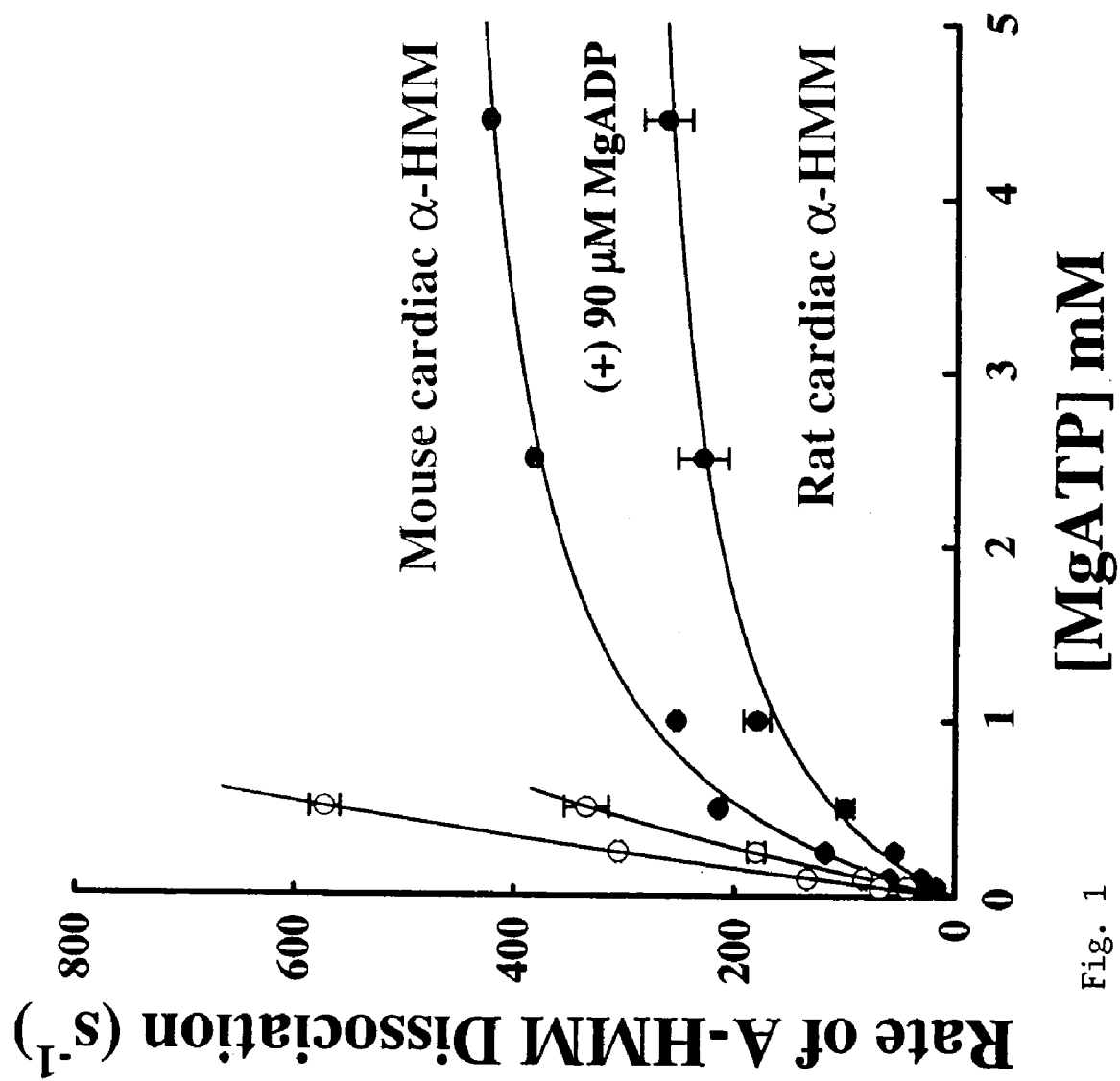
FIG. 1—Stopped-flow measurements of the dissociation of acto-HMM and acto-HMM-ADP by MgATP in rat-α (blue) and mouse-α (red) myosins. Rates of acto-HMM dissociation in absence of ADP increased sharply and were linear up to at least 500 µM MgATP. Rates of acto-HMM dissociation in presence of 90 µM MgADP show that although a plateau was reached in the two myosins, they yield rates that differ by nearly 2-fold ($K_{+5}$). The solid lines are fits to the data described in the text. In each case, filled circles represent data from experiments. The error bars represent ±one S.E.M.
Figure 5A:
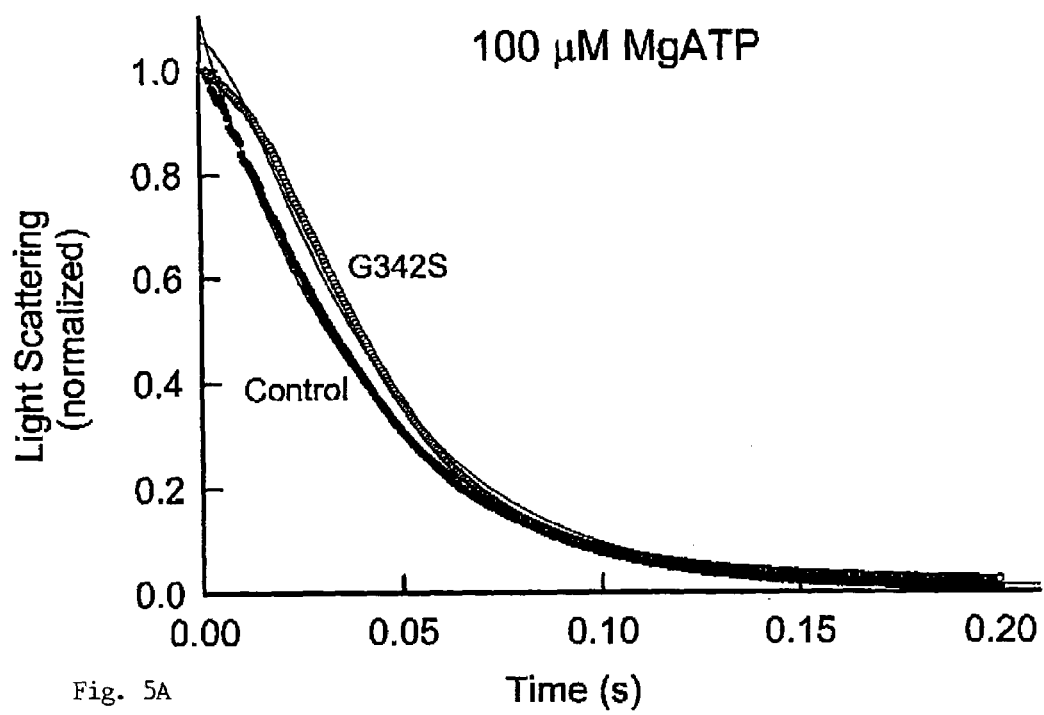
FIG. 5 (A-D)—Rates of acto-HMM and acto-HMM-ADP dissociation for wild type and mutant smooth muscle HMMs.
Figure 5B:
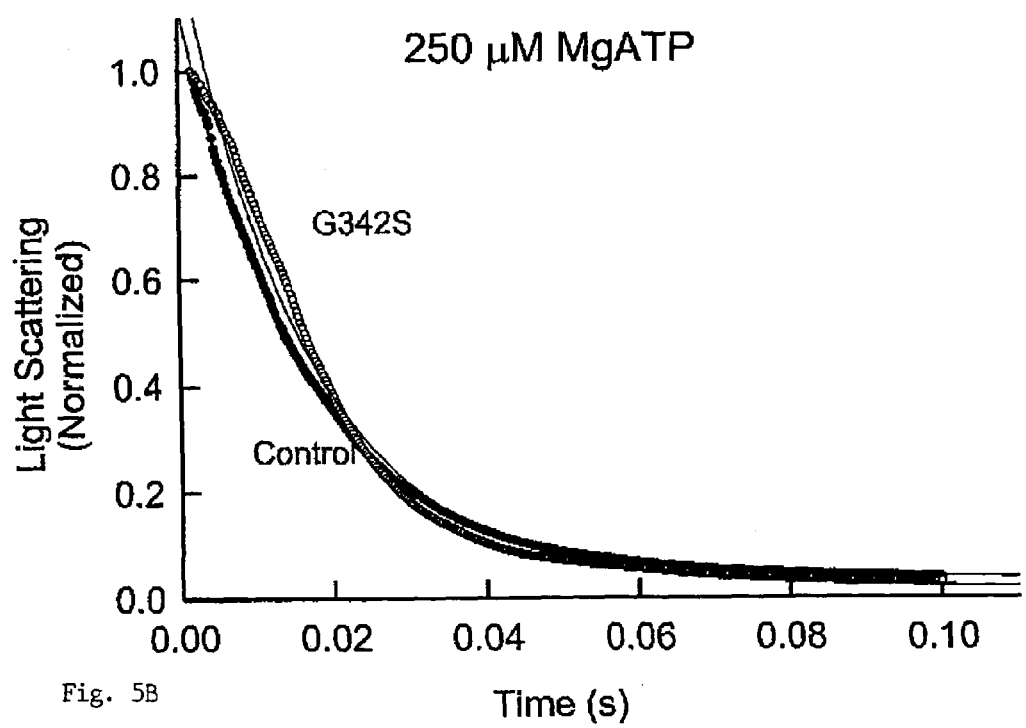
Figure 5C:
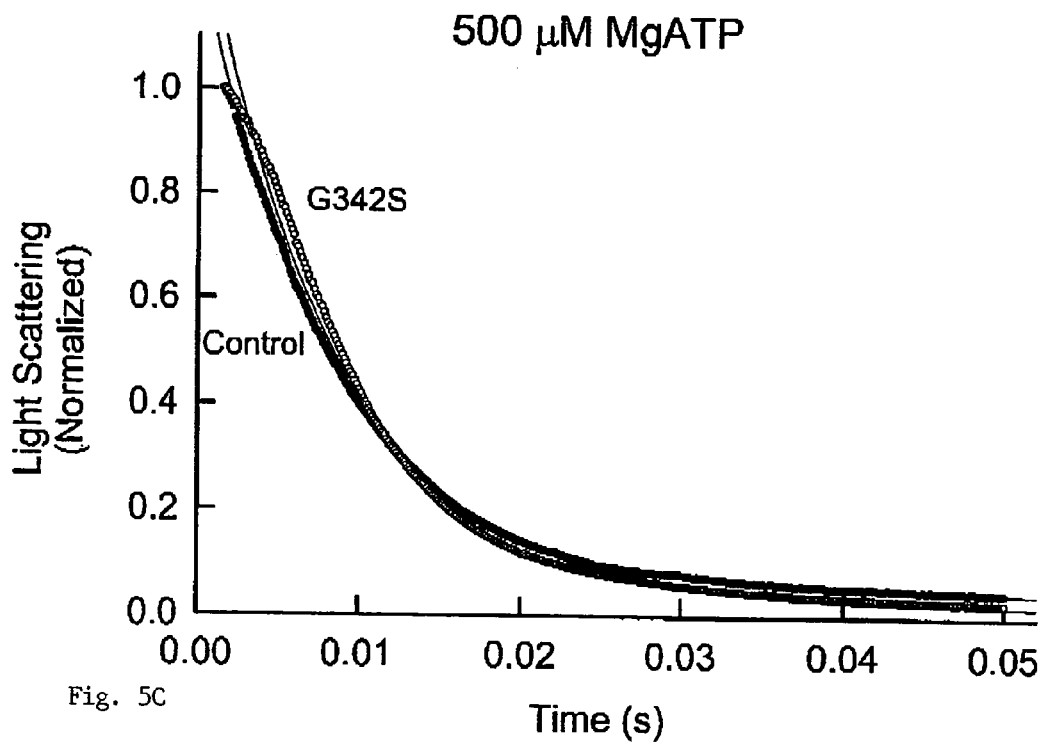
Figure 5D:
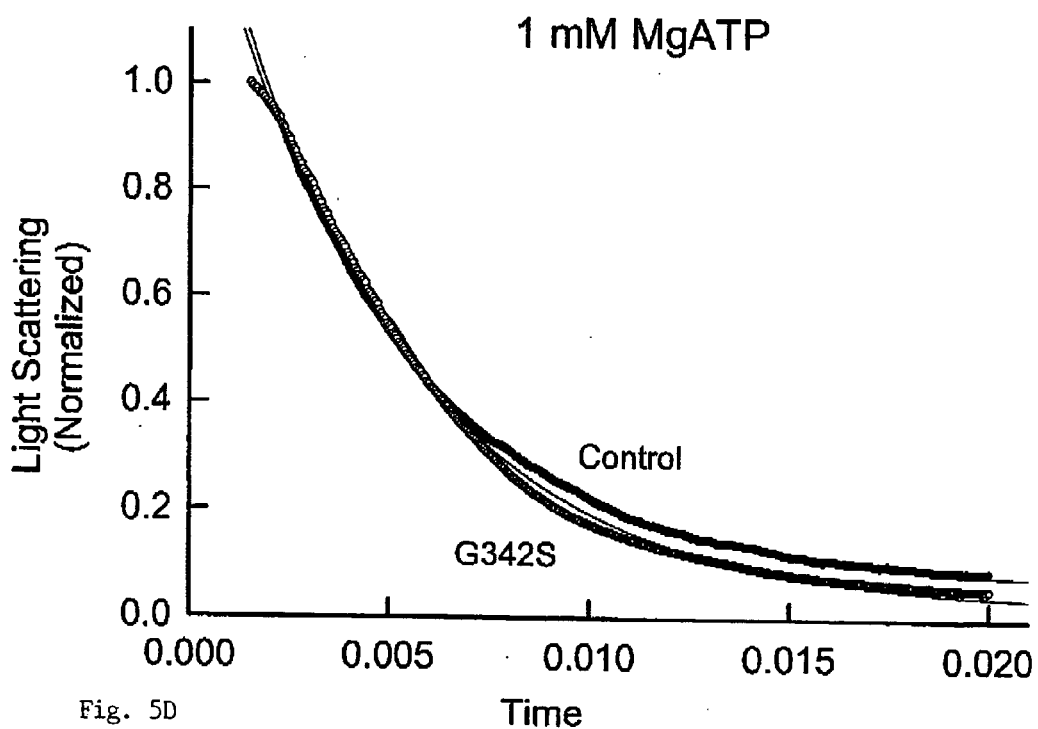

According to the present invention, any non-human animal suitable for the study of heart disease and heart failure may be used as a starting organism for the preparation of a transgenic animal of the present invention. Preferably, the transgenic model of the present invention is a mammal including, but not limited to, pigs, rabbits, primates and rodents. Most preferably, a transgenic model of the present invention is a rodent, and even more preferably, a mouse.

The preparation and uses of the transgenic animal model of the invention will be described below with particular reference to a transgenic mouse. However, the transgene and methods and uses for the transgenic mouse of the present invention, as described below in detail, can be modified and applied to any suitable mammal for the study of heart muscle disease.

According to the present invention, a transgenic mouse is a mouse that includes a recombinant nucleic acid molecule (i.e., transgene) that has been introduced into the genome of the mouse at the embryonic stage of the mouse's development. As such, the transgene will be present in all of the germ cells and somatic cells of the mouse. Methods for the introduction of a transgene into a mouse embryo are known in the art and are described in detail in Hogan et al., Manipulating the Mouse Embryo. A Laboratory Manual, Cold Spring Harbor press, Cold Spring Harbor, N.Y., 1986, which is incorporated herein by reference in its entirety. See also U.S. Pat. Nos. 4,736,866, 5,387,742, 5,545,806, 5,487,992, 5,489,742, 5,530,177, 5,523,226, 5,489,743, 5,434,340, and 5,530,179. For example, a recombinant nucleic acid molecule (i.e., transgene) can be injected into the pronucleus of a fertilized mouse egg to cause one or more copies of the recombinant nucleic acid molecule to be retained in the cells of the developing mouse. A mouse retaining the transgene, also called a "founder" mouse, usually transmits the transgene through the germ line to the next generation of mice, establishing transgenic lines. According to the present invention, a transgenic mouse also includes all progeny of a transgenic mouse that inherit the transgene.

According to the present invention, a transgene-negative littermate is a mouse that is born into the same litter as a transgenic mouse described herein (i.e., a littermate), but does not inherit the transgene (i.e., is transgene-negative). Such a mouse is essentially a normal, or wild-type, mouse and is useful as an age-matched control for the methods described herein.

The mutant αMHC transgenes according to the present invention are constructed and cloned by standard methods known in the art. Such standard methods are disclosed, for example, in Sambrook et al., 1989, Molecular Cloning: A Laboratory Manual, Cold Spring Harbor Labs Press. The reference Sambrook et al., ibid., is incorporated herein by reference in its entirety.

In the transgenic mouse described herein, the transgene includes DNA coding for a mutant αMHC including a mutation altering the kinetic properties of the respective αMHC. Preferably, the mutation is a S342G mutation in mouse αMHC which retards the motor kinetics of the αMHC and results in a transgenic mouse having reduced contractility (speed of contraction) but increased power generating capability (work capacity). In another embodiment, the transgene may be a non-mouse cardiac αMHC, preferably from a larger mammal (e.g., rat or human) which provides reduced contractility but increased work capacity. The present invention also encompasses mutant αMHC's having mutations in loop 1 which alter the kinetic properties of the mutant motor protein, preferably providing reduced contractility but increased power. Specific embodiments of such mutants are set forth in the examples below. In general, transgenic mice according to the invention will have reduced heart rates and hearts (and myocardium) which more closely resemble that of a human.

Mutant clones can be isolated using standard methods known in the art. Alternatively, DNA coding for a mutant αMHC can be synthesized by chemical synthetic methods known in the art using known sequences. The transgene may contain a single copy or multiple copies of the mutant αMHC coding sequence (in general, increasing the copy number of the αMHC coding sequence will increase expression of the encoded protein).

In addition to the nucleic acid coding for αMHC, transgenes according to the present invention are constructed to include a promoter selected to drive expression of the mutant αMHC exclusively in the heart. Preferably, the promoter is an α-myosin heavy chain promoter.

In addition to the promoter, transgenes according to the invention will contain other expression control sequences necessary or desirable for proper expression and processing of the mutant αMHC. These expression control sequences and the promoter will be operatively linked to the mutant αMHC-encoding DNA. The phrase "operatively linked" refers to linking of nucleic acid sequences in the transgene in a manner such that the mutant αMHC can be expressed in cardiac cells when the transgene is integrated into a host genome. The additional expression control sequences are well known in the art and include sequences that control the initiation, elongation, and termination of transcription (such as enhancer sequences and polyadenylation sequences).

Transgene sequences are cloned using a standard cloning system, and the transgene products are excised from the cloning vector, purified, and injected into the pronuclei of fertilized mouse eggs. Stable integration of the transgene into the genome of the transgenic embryos allows permanent transgenic mouse lines to be established. Examples of suitable techniques are further provided in the following sections that deal with specific embodiments.

Mouse strains that are suitable for the derivation of transgenic mice as described herein are any common laboratory mouse strain. Preferred mouse strains to use for the derivation of transgenic mice founders of the present invention include C57 strains, preferably C57B1/6. Founder mice are bred into wild-type mice or other suitable partners to create lines of transgenic mice to facilitate screening and establishment of stable lines.

Another aspect of the present invention is a method of using the transgenic mammals of the invention to study cardiac disease, heart muscle disease and heart failure. The characteristics of heart muscle disease and heart failure are well known. See, e.g., Heart Disease: A Textbook of Cardiovascular Medicine (5th ed., Braunwald ed., 1997).

In particular, the transgenic mammals of the invention may be used to study the molecular and cellular aspects of heart muscle disease and heart failure. For instance, a transgenic mouse of the present invention may be sacrificed, and the cells and/or tissues examined at the cellular or molecular level and compared to the cells and/or tissues from transgene-negative littermates. Examples of experiments that can be performed include, but are not limited to, morphological examination of cardiac cells; histological examination of cardiac tissues, of heart sections, of myocytes and/or of myofibrils; evaluation of cardiac myocyte DNA replication and/or expression; assays to evaluate enzyme (motor) activity both in solution and in contracting myocardium and working hearts; and assays of αMHC expression and of signal transduction. The methods of performing such experiments are standard and well known in the art.

In addition, the transgenic animals of the invention can be used to study the effects of overexpression of mutant αMHC. For instance, the effects of overexpression of αMHC on heart morphology and function, myocyte morphology and function, the expression of other molecules, the development and treatment of heart muscle disease and heart failure, can be evaluated. The methods of performing such experiments are standard and well known in the art.

Another embodiment of the present invention relates to a system in which to test drugs candidates for prevention or treatment of heart muscle disease and heart failure. In this embodiment, a transgenic mouse of the invention serves as an in vivo system to evaluate the effect of drug candidates for prevention or treatment of heart muscle disease and heart failure. Specifically, a transgenic mouse of the present invention is administered a candidate drug. The mouse is then evaluated for physiological and pathological changes that indicate the efficacy of the drug for prevention, treatment, or reduction of the rate of progression, of heart muscle disease and/or heart failure. Of particular interest are drugs that prevent the development of heart failure either as a primary disease or as a sequel to other heart diseases (such as ischemic heart disease or valvular disease) or other systemic diseases. A drug refers to any chemical compound that can be administered to an animal as an aid in the diagnosis, treatment or prevention of disease or an abnormal condition.

In addition, the transgenic mice of the invention may be used to evaluate the effects of drugs the interact with or affect αMHCs. The effects studied can include effects on the αMHCs themselves, effects on heart morphology and function, effects on myocyte morphology and function, effects on signal transduction, effects on the expression of other molecules, and effects on the development and treatment of heart disease and heart failure.

In accordance with the present invention, acceptable protocols to administer a candidate drug include the mode of administration and the effective amount of candidate drug administered to an animal, including individual dose size, number of doses and frequency of dose administration. Determination of such protocols can be accomplished by those skilled in the art, and the determination of such protocols is, in fact, another use of the transgenic mice of the invention. Suitable modes of administration can include, but are not limited to, oral, nasal, topical, transdermal, rectal, and parenteral routes. Preferred parenteral routes can include, but are not limited to, subcutaneous, intradermal, intravenous, intramuscular and intraperitoneal routes. Preferred topical routes include inhalation by aerosol (i.e., spraying) or topical surface administration to the skin of an animal. Preferred is oral administration.

According to the method of the present invention, an effective amount of a candidate drug to administer to an animal comprises an amount that is capable of preventing or treating heart muscle disease or heart failure, or interacting with or affecting αMHCs, without being toxic to the animal. An amount that is toxic to an animal comprises any amount that causes damage to the structure or function of an animal (i.e., poisonous). Prevention or treatment of heart muscle disease or heart failure can be assessed as a change (i.e., increase or reduction) in a phenotypic characteristic associated with heart muscle disease or heart failure, such change being indicative of prevention or treatment of heart muscle disease or heart failure.

Yet another embodiment of the present invention relates to the use of a transgenic mouse of the invention to study the effects of external factors on heart muscle disease and heart failure. Such factors include, but are not limited to, diet and exercise. In this embodiment, a transgenic mouse is fed a particular diet or submitted to a particular exercise regimen that is to be studied for its effect on heart muscle disease or heart failure. Such mouse is then monitored for a change in one or more characteristics of heart muscle disease or heart failure in comparison to transgene-negative littermates. For example, the effects of a low-fat diet or of moderate exercise on the development of characteristics associated with heart muscle disease and heart failure can be evaluated using the transgenic mouse model of the present invention.

Yet another embodiment of the present invention relates to a method to study heart muscle disease, heart failure, or overexpression of αMHC by breeding a transgenic mouse of the present invention with other genetically altered mice. Examples of other genetically altered mice which would be candidates for such breeding experiments include mice with manipulations in systems such as the renin-angiotensin system, calcium handling systems, cell signal transduction systems, and adrenergic nervous system. See Milano et al., Science, 264, 582-586 (1994); Gaudin et al., J. Clin. Invest., 95, 1676-1683 (1995); Iwase et al., Circ. Res., 78, 517-524 (1996); Bertin et al., Cardiovasc. Res., 27, 1606-1612 (1993); Koch et al., Science, 268, 1350-53 (1995); Samama et al., Proc. Natl. Acad. Sci. USA, 94, 137-141 (1997); Milano et al., Proc. Natl. Acad. Sci. USA, 91, 10109-10113 (1994).

Before illustrative examples of the present methods and materials are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. All publications cited herein are incorporated by reference into this document in their entirety for all purposes including describing and disclosing the polypeptides, polynucleotides, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

EXAMPLE I

Substitution of a Conserved Residue Confers Unique Kinetic Properties to Mouse α-Cardiac Myosin A. Introduction Transgenic technology has become an invaluable tool in modern science. The vast majority of transgenic models are murine, a choice that is based on the assumption that mouse provides genetic and protein backgrounds that are generally representative of mammalian systems, including human. Although this premise is likely to be appropriate in many cases, it is questionable whether it applies to all organ systems. The inventors' particular interest is the extent to which mouse cardiac myosin is a valid model for studies of human myocardial disease or more fundamental aspects of contraction. The present invention, in fact, is directed to transgenic mice better resembling the human cardiac parameters including reduced contractility and greater power generation. Such mechanical characteristics are much better matched to the much faster heart rate for mouse (approximately 600 beats per minute versus 70 for humans). Embodiments of the invention described below are anticipated to yield transgenic mice with reduced contractility, increased power, and significantly reduced heart rates, preferably 300 beats per minute or lower.

Type II muscle myosins are part of the super-family of actin-activated $Mg^{2+}$ ATPase molecular motors that drive force development and motion in muscle contraction. Each myosin is comprised of two heavy chains (MHC) and two pair of regulatory and essential light chains (MLC). Since enzymatic activity and motor function are both localized to sub-fragment 1 (S-1) of the MHC (Rayment et al., 1993), the functional diversity among myosin isoforms is predominantly determined by variations in primary sequence of the genes encoding MHC. Mammalian MHC's derive from a family of closely related isoform genes (Schiaffino and Reggiani, 1997) but only two, α and β, are expressed in the adult mammalian myocardium. In the adult, the expression of both isoforms is regulated in a tissue and species-specific manner, such that in a small rodent like the mouse, the faster α-myosin accounts for 95-100% of the total myocardial MHC's, whereas in larger mammals like the human the slower β-MHC predominates. Such differences in phenotypic profiles have long been thought to account for myocardial functional diversity across mammalian species, while no functional differences have been ascribed to the expression of analogous MHC's in different species. However, the inventors have recently shown that the kinetic properties of myosins encoded by the same MHC isoform gene but deriving from different species (e.g., pig or human β versus rat β), can exhibit greater functional differences than those between distinct phenotypes (α versus β) originating from the same species (Sant'Ana Pereira et al., 2001). This is an important result because myosins encoded by orthologous genes (e.g., rat, pig and human β MHC genes with high homology at 3'UTR and with shared protein epitopes) exhibit much greater sequence homology than myosins encoded by different genes (α versus β), implying that the functional diversity between myosin motor proteins need not be related to overall levels of sequence homology. Consistent with these observations, studies of familial hypertrophic cardiomyopathies (FHC) have shown that that a single point mutation can dramatically alter the kinetic properties of myosin, a factor that appears to be instrumental in the development of the disease (for review, Lowey, 2002). Thus, the functional impact of single substitutions must be carefully assessed on a case-to-case basis.

The best approach to assess whether a given myosin is representative of its mammalian counterparts is to perform comparative structure-function analyses between that myosin and its closest related isoform. Such an approach involves minimal sequence divergence, which in turn allows identification of which variant residues in otherwise conserved regions are likely to confer unique functional differences. For example, amino acid sequence comparisons of mammalian cardiac myosins indicated that the isoform most closely related to mouse α-myosin is rat α-myosin, which differs by only 3 non-conservative single substitutions in sub-fragment 1 (S-1). Importantly, the inventors observed that although myocardial myosin is comprised almost exclusively of α-MHC in both species, resting heart rate is considerably faster in the mouse than in the rat. Since a strong correlation appears to exist between speed, power, resting heart rate and MHC phenotype, it seemed likely that the two myosins would exhibit marked differences in function despite differing by only three amino acids. To test this idea, purified myosin and skinned cardiac myocytes from both species were used to examine the kinetics of actomyosin interaction by stopped-flow and mechanical assays. From the three non-conservative substitutions, one is in a residue (G342S, chicken skeletal numbering) that is highly conserved among myosin II family members, including *Dictyostelium dictoideum* (DM), scallop, chicken smooth muscle (SmM) and chicken skeletal muscle (SkM), for which there are also 3-D atomic structures. To investigate the role of the G342S substitution, recombinant SmM HMM molecules were engineered to express the S substitution for G typical of mouse α myosin. The structural consequences of the substitution were also analyzed using the coordinates of the 3D SmM structure. The inventors concluded that the unusual G342S substitution confers unique kinetic properties to mouse α myosin. Indeed, the G342S substitution serves as a basis for one preferred embodiment of a mutant αMHC transgene having alterered kinetic parameters that significantly mimic the slower heart rate of larger mammals, including humans. In general, the ser at position 342 in mouse α myosin is mutated to a gly and the mutant construct then introduced into a mouse line using standard transgenic techniques. The resulting transgenic mouse is predicted to have slower speed, greater power and reduced heart rate better resembling larger mammals.

B. Methods

Experimental Animals. Rats (Sprague Dawley; 3 monh, n=20) and mice (CD1 Crabe strain, 4 month old, n=30) were housed in temperature- and light-controlled quarters according to strict guidelines established by the University of Wisconsin Animal Care Committee. Rats were made hyperthyroid by means of daily intraperitoneal injections of levothyroxine (0.2 mg/kg) for 30 days to obtain hearts expressing nearly 100% α-MHC. The same procedure was not required for mice because the myocardial phenotype in CD1 strain is comprised exclusively the α-MHC phenotype. Prior to organ collection, all animals were anaesthetized in a glass bell jar containing room air and 4% methoxyflurane (deep anesthesia was confirmed) and subsequently sacrificed by surgical introduction of pneumothorax.

Tissue preparation. The left ventricle of each heart (mice n=32; rat n=20) was carefully removed and immediately processed to generate samples for protein purification (Sant'Ana Pereira et al., 2001a). Samples were also prepared under sterile conditions for RNA extraction (n=3). Here, muscle samples were homogenized in a polytron and immediately processed (see below). Additional hearts (n=8) from both species were collected and enzymaticaly digested to obtain cardiac myocytes for mechanical studies (Sant'Ana Pereira et al., 2001a). Skinned myocytes were stored on ice for use on the same day.

Myosin phenotypes and protein purification. MHC content was characterized by pulse-electrophoresis, using 16 cm SDS-polyacrylamide gels (Sant'Ana Pereira et al., 2001b). The gels were run for 48 hours using on/off cycles lasting 20 seconds each, using standard conditions of current (13 mA) and temperature (10° C.). The gels were then silver stained. Further SDS-PAGE analysis was performed to assess the purity of the extracted myosin, as well as the specificity of chymotryptic-generated HMM fragments (see below). This analysis was done in 12% separating polyacrylamide (1% bisacrylamide cross-linking) mini-gels, which were subsequently stained with coomassie brilliant blue.

Amino acid sequence composition and alignments. Amino acid sequence compositions of the α-MHC isoforms of rat and mouse were initially obtained from previously resolved sequences (NCBI accession numbers: M76601/mouse-α and X15938/rat-α). To rule out the possibility of strain variability in amino acid sequence composition in the two species used in this study, PCR products amplified from cDNA originating from the same animals were cloned (pBlue script) and sequenced to determine the deduced amino acid composition of the two α-MHC isoforms. cDNA's were obtained by reverse transcription (Invitrogen) of the mRNA fraction of purified total RNA (Trizol™). Amplification of products was performed using specific primers. The deduced amino acid sequences were then compared to those previously deposited in "NCBI" and "Swiss Prot" and further aligned with a variety of published sequences of various type II myosins, including those with known 3-D structures obtained by x-ray crystallography.

Unloaded shortening velocity ($V_0$). Mechanical $V_0$ was measured in maximally activated myocytes using the slack test method described by Strang et al., (1994). Once steady tension was achieved in activating solution, the myocyte was slackened by 12-17% of initial length, measured at a sarcomere length of 2.25 μm. The time between imposition of a slack step and redevelopment of force was measured by fitting a horizontal line through the tension baseline. The maximum slack imposed was such that sarcomere length did not shorten below 1.90 μm, which is about 0.1 μm greater than the length at which distortion due to mechanical restoring forces within the myocytes is likely to occur (Strang et al., 1994; Fitzsimons et al., 1998). Length change (as percent initial length) was plotted versus duration of unloaded shortening (ms), and unloaded shortening velocity ($V_0$) was determined from the slope of a line fitted to the data by linear regression analysis. Data were considered valid when the regression coefficient was >0.95.

Purification of native myosins from rat and mouse hearts and generation of HMM. Myosin purification was performed from frozen muscle powder as previously described (Sant'Ana Pereira et al., 2001a). In brief, frozen powder was gradually mixed with a skinning buffer to pellet the myofibrils that were subsequently used for purification of actin and myosin. Following sedimentation, the acto-myosin pellet was recovered by centrifugation and re-suspended in an ATP containing solution to remove contaminating actin. Myosin molecules were then recovered by precipitation and digested to HMM by addition of TLCK-treated chymotrypsin (20 μg/ml). This procedure was performed under low temperature-dialysis using dialysis slides (10,000 Da pore) to remove contaminant nucleotide from the samples. The chymotryptic digestion was stopped after 7 hours (1 mM PMSF) and the samples were further dialyzed (2×4 hours against 4 l of 25 mM MOPS, 2 mM $MgCl_2$, 2 mM DTT, 1 mM $K_2$-EGTA, pH 7.3) to precipitate undigested myosin and light meromyosin, while reducing contaminating nucleotide to <0.1 μM. HMM was recovered by centrifugation and supplemented with 100 mM KCl to yield total ionic strength of 120 mM.

Purification of actin and generation of F-actin. Actin was prepared as described by Pardee and Spudich (1982) from acetone powder processed from the residue of rabbit muscle after myosin extraction. A 120 μM stock of f-actin was dialyzed against 25 mM MOPS, 100 mM KCl, 2 mM $MgCl_2$, 2 mM $K_2$-EGTA, 2 mM DTT, pH 7.3.

Mutagenesis, expression and purification of recombinant smooth muscle myosins. Chicken smooth muscle (SmM) cDNA corresponding to the HMM portion of myosin (Yanagisawa et al., 1998) was used as a template for site-directed mutagenesis. One single point mutation, mimicking the naturally occurring Gly-to-Ser substitution in the mouse-α myosin was introduced in the corresponding G343 residue of the smooth myosin sequence (G342S in chicken SkM) using methods described previously (Kunkel, 1985). The mutant was confirmed by DNA sequencing. In this study, the mutant SmM is designated as G343S in contrast to G342S (SkM numbering) when referring to the cardiac isoforms. The choice of SkM numbering when referring to the cardiac isoforms is based on the facts that (1) the $NH_2$-terminal deletion in rat α-MHC, absent in the mouse α-MHC, would change the numbering of the two myocardial isoforms, and (2) in the absence of characterized 3D structures of mammalian cardiac myosins, the SkM structure is the closest to that for the cardiac myosin sequences.

Recombinant baculovirus was isolated using previously reported methods (O'Reilly et al., 1992). Sf9 cells were then co-infected with recombinant virus coding for a truncated heavy chain fragment similar to the chymotryptic HMM (1175 amino acids) and another virus coding for smooth muscle regulatory light chain (Trybus and Chatman, 1993) and essential light chain (Nabeshima et al., 1987). Isolation of the expressed protein (wild type and mutant) was achieved by chromatography of fusion-tagged HMM on an anti-flag affinity column (Trybus et al., 1998). The yields of wild type and mutant HMM's were similar (~5 mg/liter culture cells), and the properties of proteins from independent preparations were invariant. Immunoblots of glycerol gels (Perry and Perry, 1975) were used to verify complete phosphorylation (Trybus, 1994) of the regulatory MLC in all cases.

Kinetics of ATP binding and ADP dissociation using stopped-flow. For transient kinetics, the rates of MgATP-induced dissociation of acto-HMM and acto-HMM-ADP were measured in a micro-volume Stopped-Flow Reaction Analyser SX.18MV (dead time of 1.6 ms) with Pro/Kineticist (Applied Photophysics). In all experiments the temperature of the drive syringes, mixer and observation cell was regulated to 15° C. using a refrigerated water bath. The rates of dissociation of acto-HMM in the presence and absence of MgADP were monitored by changes in light scattering at 340 mn (Siemankowski & White, 1984). MgATP-induced dissociation of acto-HMM was initiated by rapidly mixing a solution of 4 µM actin, 2 µM HMM, and 1 µM AP$_5$A in 100 mM KCl, 25 mM MOPS, 1 mM EGTA, 1 mM MgCl$_2$, 1 mM DTT, pH 7.4, with one containing 0.02, 0.05, 0.1, 0.2, 0.5, 1.0, 2.0, 5.0 or 10.0 mM MgATP in identical salts (Sant'Ana Pereira et al., 2001a). To measure the rate of MgADP dissociation from acto-HMM, 180 µM MgADP was added to the acto-HMM-AP$_5$A solution before mixing with the same ATP concentrations as above. Exponential fits to the time course of light scattering were performed using software routines supplied by the device manufacturer. Typically, the rates of 3-4 stopped flow records were averaged to obtain a rate representative of a given MgATP concentration.

Structural analysis for the impact of the substitutions. To assess the impact of the substitutions between rat α and mouse α-myosins we began our analysis by retrieving the 22 crystal structures deposited in the Protein Data Bank (PDB). These were subsequently superimposed using Modeller (version 6v1), a computer program that models 3D structures of proteins by satisfaction of spatial restraints (Marti-Renom, 2000). An initial family alignment of all structures and sequences was prepared using the default parameters suggested by Modeller. The structural alignment was optimized by exclusion of both the NH$_2$-terminus and the converter domain. Graphic visualization and further analysis of the superimposed structures were then performed with Turbo (Roussel and Cambilau, 1989) using either a large number of structures or simply the most representative.

C. Results

Mouse and rat phenotypes. Characterization of MHC phenotypes using pulse-PAGE indicated that the predominant myosin band in the two species exhibited the migration mobility characteristic of previously identified α-MHC in both species (Sant'Ana Pereira et al., 2001b). In rats, this was confirmed by Western blot analysis using a characterized anti-α MHC mouse monoclonal antibody as well as by immunohistochemistry. These results confirmed that hyperthyroidism successfully converted the myocardial phenotype to nearly 100% α-MHC.

Unloaded shortening velocity. Measurements of mechanical $V_0$ in skinned individual myocytes yielded marked differences between the two species. In rat ventricular myocytes, $V_0$ was nearly 50% slower (2.5±ML/s; mean±SD, n=8) than in mouse ventricular myocytes (4.26±ML/s; mean±SD, n=5). Myocyte attachment to the apparatus yielded consistently low compliances, since sarcomere length decreased by 3% or less during the transition from rest to maximal activation. Thus, the observed differences in mechanical $V_0$ were not due to methodological artifact. Further, since $V_0$ is thought to provide an indirect measure of the rate of ADP dissociation, the differences in this parameter provide the first indication that the kinetic properties vary between the two α-myosins.

Kinetics of acto-HMM and acto-HMM-ADP dissociation in mouse α and rat α HMMs. Estimates of the kinetics of ATP binding to and ADP dissociation from rat and mouse α cardiac acto-HMM were obtained by measuring the ATP-dependent rate of acto-HMM dissociation in the presence and absence of added ADP (FIG. 1). The use of ADP as a competitive inhibitor of ATP binding at the active site allows estimation of ADP off rates.[26] The reaction for the decrease in light scattering is given in mechanism 1:

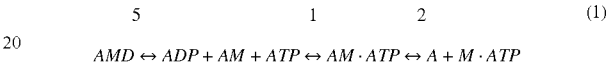

$$AMD \leftrightarrow ADP + AM + ATP \leftrightarrow AM \cdot ATP \leftrightarrow A + M \cdot ATP \qquad (1)$$

FIG. 1 shows the decrease in light scattering upon mixing MgATP with acto-HMM (15° C. and 120 mM ionic strength), which effectively reports dissociation of acto-HMM. The data were well fit using a single exponential, meaning that (1) contaminating ADP (from the purification procedure) was removed by prolonged dialysis and (2) both samples were comprised of a single MHC isoform.

When ADP is added to an acto-HMM solution prior to mixing with MgATP, the reaction shown in mechanism 1 occurs in its entirety. If the release of ADP from acto-HMM, $k_{+5}$, is much slower than the rate of acto-HMM dissociation by ATP ($K_1 \cdot k_{+2}$[MgATP]), then at high [MgATP] the rate of decrease in light scattering will be limited by and equal to $k_{+5}$. At low [MgATP] (when $k_{+5} > K_1 k_2$[MgATP]), MgADP reduces the $k_{obs}$ by competing with MgATP for binding to acto-HMM, thereby decreasing the fraction of acto-HMM available to pass through steps 1 and 2. Thus, at low values of [MgATP], $k_{obs}$ will be small and will rise toward $k_{+5}$ as [MgATP] is increased. The rates of acto-HMM-ADP dissociation were accurately fitted by a single rate of dissociation because the amount ADP added to the acto-HMM in each case was selected to produce the large fraction of acto-HMM as acto-HMM-MgADP prior to mixing with MgATP.

The rates of acto-HMM dissociation were also plotted as functions of [MgATP] in the absence and presence of MgADP, where the dots are observed rates and solid lines are fits to the data. For acto-HMM dissociation by MgATP alone, the data for both cardiac HMM's could be resolved by linear fits. This fit yielded $K_1 \cdot k_{+2}$ of 13±0.3×10$^5$ M$^{-1}$s$^{-1}$ and $K_1$ of 3400±70 M$^{-1}$ for mouse α-HMM and $K_1 \cdot k_{+2}$ of 8.2±0.4×10$^5$ M$^{-1}$s$^{-1}$ and $K_1$ of 1200±480 M$^{-1}$ for rat α-HMM ($R^2$=0.999). Conversely, the rates of acto-HMM dissociation in the presence of MgADP showed an obvious plateau of the dissociation rate. Here, the analysis yielded $K_{+5}$ values of 404.0±21 s$^{-1}$ for mouse α-HMM and 245.3±15.4 s$^{-1}$ for rat α-HMM. To obtain an estimate of $k_{-5}$, the inventors used the rates of $K_1 k_{+2}$ (and assumed that $k_{+2}$=2×10$^4$ s$^{-1}$) and asymptote for $k_{+5}$ (404 s$^{-1}$ and 245.3 s$^{-1}$) in reaction 1. Using $K_1 k_{+2}$ and $k_{+5}$, the inventors computed the rates of rat acto-HMM-MgADP dissociation using simulations of equation 1 and found that the rates observed at different [MgATP] were well predicted if $k_{-5}$=5×10$^6$ M$^{-1}$s$^{-1}$ (the solid line in FIG. 1 gives the predicted rates). The results indicate that while the ATP-induced rate of acto-HMM dissociation is not rate limiting for either isoform, the rate of ADP dissociation differs by nearly 2-fold. Thus, the inventors concluded that the substitutions between rat and mouse α myosins do not affect nucleotide-binding properties but do confer different rates of nucleotide-release in the two motor proteins.

Sequence divergence, location of the substitutions in 3D Atomic structures of myosin and predicted functional impact. Amino acid sequences corresponding to the S-1 region of rat and mouse α MHC's were deduced from PCR-amplified cDNA's. Chromatograms yielded reproducible data (12 clones of each) that were identical to the sequences previously deposited in gene bank. Sequence comparison analysis recognized four mismatches between the two isoforms (SkM numbering): (1) a deletion in residue 12 (A14 in SkM) and a conserved substitution (R16Q, SkM numbering) at the $NH_2$ terminal sub-domain; (2) a single substitution G342S (SkM numbering); (3) a single substitution R741G (SkM) in the converter domain (FIG. 2). The locations of the substitutions were visualized (FIG. 3A) using the backbone atomic structure of chicken skeletal myosin (S-1) (Rayment et al., 1993) because among all available 3D structures of myosin (crystal structures of mammalian cardiac myosins are not available), SkM has the greatest sequence homology with the two cardiac myosins studied herein.

Two distinct but complementary approaches were used to determine which of the variant residues were the most likely candidate(s) for the kinetic differences between rat α and mouse α HMM-s. First, the inventors assessed the structural impact of the different substitutions using the 22 crystal structures of myosin available in the Protein Data Bank (PDB). Since these structures derive from different sources such as scallop, SkM, SmM, and DM, and some of these represent three different conformational states of myosin, the inventors used differences both in conformation and in structural backbone due to variations in sequence composition to assess the impact of each substitution. The superimposed structures (note that for superimposition, the variable regions in the structures were excluded in the calculations, e.g., in SkM only residues 80 to 710 were included) indicated that (1) the region of the motor domain comprising G342 was highly conserved in the different structures and (2) both the $NH_2$-terminal sub-domain (up to residue F78 in SkM) and converter (after residue 721), as well as the region encompassing switch-2 and relay (D463 to S650) were highly variable. These observations are consistent with previous analyses (Gulick and Rayment, 1997; Dominguez et al., 1998; Houdusse et al., 1999; Geeves and Holmes, 1999). To simplify and improve the impact analysis for each substitution, three structures representative of three different states of myosin were selected (FIG. 3B-C): (1) SkM without nucleotide (PDB code: 2mys) representative of state I or ATP state (Rayment et al., 1993; Bauer et al., 2000) which exhibits high homology with rat and mouse α myosins; (2) SmM complexed with $MgADP.AlF_4$ (with the ELC), representative of state II or pre-power stroke (Dominguez et al., 1998); (3) scallop structure complexed with MgADP, designated as state III and believed to be a second ATP state that is transitional between the ATP state I and the pre-power stroke conformation in state II (Houdusse, 1999). The location and behavior of the variant residues in the three conformational states of myosin are shown in FIG. 3 (A-C).

In the second approach, sequence alignments were performed to determine how prevalent the substitutions between rat-α and mouse-α are among myosin II members. This analysis yielded a number of important observations: (1) although the $NH_2$ terminal sub-domain is highly variable among type II myosins, the deleted residue 14 (SkM numbering) in rat α myosin is occupied by a conserved Ala in myocardial myosins with both faster (e.g., mouse α) or slower (human or rat β) nucleotide turnover kinetics (FIG. 4A); (2) residue 741 (ChSK numbering) is variable among myosin II isoforms but is conserved in mouse α (R741; G741 in rat α) and rat β (FIG. 4B); (3) G342 is highly conserved among myosin II isoforms except in mouse α, where it is replaced by Ser (FIG. 4C).

Recombinant wild type and mutant smooth muscle HMMs. Amino acid composition of the recombinant wild type (SEQ ID NO:1) and mutant (SEQ ID NO:2) smooth muscle generated in this study were confirmed by DNA sequencing. The expressed mutation of G343S occurs in an otherwise conserved residue.

```
WT       Ch Sm    341    I M G F T E E E Q T
                         (SEQ ID NO:1)

Mutant   Ch Sm    341    I M S F T E E E Q T
                         (SEQ ID NO:2)
```

Kinetics of acto-HMM and acto-HMM-ADP dissociation in wild type and mutant smooth muscle HMMs. The rates of acto-HMM and acto-HMM-ADP dissociation for the wild type and mutant smooth muscle HMM-s were assessed under conditions identical to those previously described for rat and mouse α-HMM's. Both proteins exhibited a decrease in light scattering upon mixing with MgATP (15° C. and 120 mM ionic strength), which effectively reports dissociation of acto-HMM. However, although the decrease in light scattering for wild type was well fitted by a single exponential over the entire range of [ATP], that was not the case for the mutant G343S. This phenomenon, illustrated in FIG. 5(A-D), shows that the dissociation of the mutant HMM upon MgATP binding involves at least one extra event as confirmed by the requirement for double exponential fits to the data. Importantly, both rate constants were ATP-dependent indicating that the two phenomena are functional events not caused by denatured protein.

When acto-HMM is rapidly mixed with MgATP, only steps 1 and 2 in equation 1 occur. However, in most myosins these two events cannot be distinguished from each other and so $K_1 \cdot k_{+2}$ is resolved by a single exponential fit. For the mutant G343S, $K_1 \cdot k_{+2}$ comprised at least two distinct events which were resolved by double exponential fits to the data. For all [ATP], the second exponential for mutant HMM yielded rates that were identical to those obtained by the single exponential fits for the control wild type. This indicates that the second event in acto-HMM dissociation for the mutant corresponds to $K_{+2}$, and thus the inventors concluded that introduction of the S343 mutation altered the nucleotide-binding properties of SmM.

The rate of ADP dissociation from acto-HMM is invariably much slower than the rate of acto-HMM dissociation by ATP ($K_1 \cdot k_{+2}$[MgATP]), which can be characterized in stopped-flow using light scattering or fluorescence assays. Light scattering measurements, as opposed to fluorescence measurements (e.g., with pyrene label) report weak-binding events of the acto-myosin complex. In such a case, the resulting signal for $K_{+5}$ comprises more than one chemical transition (see eq. 1). Here, $K_{+5}$ can be accurately measured using this method because $K_1 \cdot k_{+2}$ is not rate limiting, occurring so rapidly that $K_{max}$ cannot be measured (need to be estimated). At low concentrations of MgATP, $k_{+5}$ is faster than $K_1 \cdot k_{+2}$[MgATP] meaning that MgADP reduces the fraction of acto-HMM available to pass through steps 1 and 2. If $K_1 \cdot k_{+2}$ is constrained, one would expect that the rates for acto-HMM in presence of ADP are affected by this phenomenon, which is what the inventors observed, i.e., the traces for mutant HMM produced double exponential decays similar to those obtained for acto-HMM dissociation by MgATP alone (no ADP added). However, with increasing concentrations of MgATP, the reactions become faster so that the fraction of the signal corresponding to $K_1$ (even limited in this case) becomes progressively smaller until it eventually disappears. For the mutant G343S, the inventors no longer observed a lag in light scattering at [ATP] of 2.5 mM and higher, so that the light scattering is a single exponential and the rate of acto-HMM-ADP is be limited by and equal to $k_{+5}$. Importantly, $K_{obs}$ for acto-HMM-ADP dissociation against 2.5 and 5.0 mM MgATP was identical for both mutant and wild-type SmM HMM's, yielding rates of 46 $s^{-1}$. Thus, it appears that the G343S mutation did not affect the nucleotide-release properties of the motor protein.

D. Discussion

The inventors have demonstrated significant kinetic differences between rat α and mouse α myosins. Using stopped-flow methods, the rate of acto-HMM-ADP dissociation was nearly 2-fold faster for mouse α myosin than for rat α myosin, which was consistent with the differences obtained in myocyte mechanical $V_0$. Since the magnitude of the differences between mechanical $V_0$ and rate of ADP dissociation in solution were identical, the inventors' results are consistent with the notions that (1) the rate of ADP dissociation is the rate limiting step for $V_0$ (Siemanknowski et al., 1985) and (2) myofilament proteins other than myosin did not significantly affect mechanical $V_0$ because stopped-flow methods were performed using unregulated f-actin. Thus, the differences in kinetic properties reported were entirely due to properties intrinsic to the two myosins.

Myosin molecules consist of two heavy chains and two pairs of MLC's. Although MHC is the single most important determinant of mechanical $V_0$, previous studies in single skeletal muscle fibers showed that the MLC composition also played a modulatory role in the setting of this parameter (Moss et al., 1992; Botinelli et al., 1993; Sweeney et al., 1995). Since mechanical $V_0$ correlated well with the rates of ADP dissociation ($K_{+5}$) in stopped-flow, species-specific differences in MLC composition between rat α and mouse α myosins could be thought to have contributed to the kinetic differences of these two motor proteins in both preparations with intact myofilaments and purified proteins used in solution biochemistry (stopped-flow). Recently, the inventors used stopped-flow analysis to examine the effects of the MLC composition on kinetics of myocardial myosins. Using ventricular (MLC 1v) and atrial (MLC1a) HMM molecules deriving from pig and rat hearts the inventors showed that, in presence of a standard MHC phenotype, the rates of ADP dissociation were identical within each species. Furthermore, in another study, the inventors showed that partial replacement of the endogenous MLC in myosins obtained from hypothyroid rat soleus and heart muscles composition by that purified from pig ventricles also failed to produce measurable differences in acto-HMM interaction kinetics relative to controls (Sant'Ana Pereira et al., 2002). Taken together, these results indicate that the variability in MLC composition among mammalian cardiac myosins does not play a major modulatory role in kinetics of ADP dissociation, at least in solution. Consequently, the inventors conclude that the kinetic differences reported here between rat α and mouse α myosins were determined by intrinsic differences in primary sequence of the MHC in both species. The deduced amino acid sequence composition for the S-1 region of rat and mouse α MHCs, recognized the presence of only four substitutions, three of which non-conservative. This means that one or more of these three substitutions must play a remarkable role in speeding up myosin kinetics.

Assessing the Functional Impact of the Variant Residues

Substitutions at the amino terminus: deletion at residue 13 and R15Q (ChSK). Amino acid sequence comparison indicated that the NH2-terminal sub-domain is highly variable among myosins II (FIG. 4A). Since mutagenesis studies targeting residues in this region are yet to be produced, the functional impact of such variability needs to be estimated from structural data. Alignment of superposed 3D structures (FIG. 3B) confirmed the presence of high structural polymorphism in this region among myosins. Remarkably however, the inventors observed that such high structural variability does not introduce additional intra-molecular interactions between residues of the NH2 terminus with the rest of the protein, in any of the myosin structures, including the scallop, which exhibits an unusual number of deletions in this sub-domain. Furthermore, the structures indicate that the NH2 terminal sub-domain of the molecule becomes conserved is all 3D structures of myosin after residue ~78 (ChSK) (see FIG. 3B), suggesting that the sequence composition of this sub-domain does not appear to have further structural repercussions. Thus, either substitution or deletion of a single residue in this highly flexible region (due to the lack of interactions) appears to be unlikely to play an active role in regulation. Consequently, the inventors found the $NH_2$-terminal substitutions between rat α and mouse α myosins to be improbable determinants of the kinetic differences reported here. Consistent with this contention, results from the sequence comparison analysis indicated that the deleted residue in rat α myosin is Ala in mouse α and also in human β and rat β, two myosins with much slower kinetics of ADP dissociation.

Substitution 741 in the converter domain. Substitutions in the converter, unlike those at the NH2 terminus, have long been believed to play an important regulatory role in myosin kinetics. Initially, structural studies indicated that the converter domain is relatively unconstrained changing greatly between states (Fisher et al., 1995). These changes are accompanied by simultaneous changes in the orientation of the lever arm (Dominguez et al., 1998), in a series of domain movements thought to be coupled to nucleotide induced conformational change in the active site (Gulick & Rayment, 1997; Dominguez et al., 1998). Subsequent site-directed mutagenesis studies have confirmed the role of the converter in conferring kinetic modulation to myosin. Whil, substitution of the entire converter sequence by domain swapping affected different kinetic properties of the indirect flight muscle of *Drosophila* (Swank et al., 2001), substitution of a single amino acid produced recombinant smooth muscle HMM molecules with a faster rate of $P_i$ release (Yamashita et al., 2001). The findings of Yamashita and co-workers are particularly important for this study in that they indicate that the converter domain is highly sensitive to the type of side chain introduced, so that one single substitution could be sufficient to tune differently the kinetics of the molecule. Thus, the inventors initially regarded the R741 G substitution as a candidate for the different tuning of ADP release rates between mouse and rat α myosins. However, analysis on the 3D structures representative of the three states of myosin indicated that residue 741 (ChSK-750 SM) is located at the surface of a α-helix and it is not directly involved in interactions with other residues of the molecule (FIG. 3C). Although the structures do not provide any obvious indication as to the role of this residue, it must be noted that the existing 3D atomic structures of myosin are all representative of actin-free states. Therefore, they may not be representative of the conformations associated with product release (Volksman et al., 2000). In fact, since position 741 can be occupied by a residue with a basic side chain, such as Lys or Arg (ChSK and other mammalian myosins; FIG. 4B), or Q (in Dicty), differences in charge and size of the side-chain in the G741R substitution may be relevant. Furthermore, the presence of Gly at this position could also be structural and functionally significant because this residue can adopt values otherwise forbidden in the Ramachandran plot for the other amino acids. Although the inventors do not dispute that many factors point toward the functional importance of this substitution, sequence comparison analysis contradicts such possibility because R741 (mouse-α) is also present in rat-β and, among small rodents, is the only amino acid that is variant in an otherwise highly conserved converter domain. Thus, if this substitution played a dramatic effect in speeding up the rate of ADP dissociation in the mouse-α myosin(HMM) comparatively to rat-α myosin (HMM) one would not expect rat-β HMM to dissociate ADP at a >3-fold slower rate (Sant'Ana Pereira et al., 2001) than mouse-α HMM and at 2-fold slower rate than the rat-α HMM (manuscript in preparation). Interestingly, the inventors observed that the ATP cleavage rate in mouse-α is slower than in rat-α HMM. It is therefore possible that this substitution modulates other kinetic steps of the cross-bridge cycle such as the rate of actin-binding or even phosphate release. In fact, single point mutations in the converter have been previously shown to affect the rate of $P_i$ release without altering the rates of ADP release (Yamashita et al., 2001).

Substitution 342 in the a-helix close to the lip of the binding pocket. Unlike the remaining substitutions between rat-α and mouse-α myosins, the G342S mutation is unique among vertebrate type II myosins (FIG. 4C). The expression of Ser in this otherwise highly conserved Gly residue suggests that such unusual substitution could confer unique kinetic properties to the mouse α myosin. Thus, a vast number of parameters were analyzed to characterize this substitution. The secondary structure assignment using "procheck" indicated that this residue connects two differently oriented helices, an observation confirmed by analysis of characterized 3D structures of myosin. In all 22 structures, G342 (ChSK; G343 Sm) is located in a tight turn in between two adjacent helices that connect the lip of the binding-pocket (and in proximity to switch-1) to the outer groove of the actin-binding site (FIGS. 6, 7). Interestingly, structural analysis did not detect changes in this region for the three actin-free states of myosin. However, recent low-resolution structures of acto-myosin revealed that the helices connected by G342 undergo conformational change upon transition from the ADP state to the rigor state (Volksman et al., 2000; see FIG. 3), probably in association with movements of the upper 50KDa sub-domain that close the cleft. In many proteins, Gly residues are often present in tight turns, working as "pivots" that confer flexibility to a given region. Hence, it appears that G342 could be strategically positioned to play a functional role in myosin function.

Assessing the role of G342S substitution in mutant recombinant Sm HMM molecules. Since G342 (G343 Sm) is highly conserved among type II myosins, the inventors reasoned that the Ser substitution in any myosin comprising the conserved Gly should sensor its functional impact on kinetic regulation. With that in mind, the inventors produced mutant Sm HMM molecules engineered to express the G342S (G343S in Sm) substitution seen in mouse α MHC. Expression of this mutation in Sm offered the additional advantage of enabling a detailed assessment of its structural impact in the already characterized Sm 3D atomic structure (Dominguez et al., 1998).

Characterization of the mutant in stopped-flow confirmed that the G342 (G343 Sm) is functionally significant since its substitution by Ser alters the kinetic properties of Sm myosin. Here, the rates of acto-HMM dissociation upon mixing with MgATP comprised two distinct events in the mutant: (1) an initial exponential decay that could be characterized as a lag comparatively with the wild type and (2) a second exponential decay, which yielded rates identical to those obtained for the control wild type. The ATP induced rates of acto-HMM dissociation are almost invariably resolved by a single exponential fit in most myosins (i.e. as single event), even thought they comprise two separate events ($K_1 \cdot k_{+2}$, $K_{+1}+K_{-1}$ and $K_{+2}$ see eq. 1). Since the second component of the dissociation fit for the mutant yielded rates identical to the single exponential decay observed for the wild type, it does appear that $K_{+1} \cdot K_{-1}$, not $K_{+2}$ was differently constrained by introduction of the mutation. This was also confirmed in the kinetics rates of ADP release at low ATP concentrations in which the light scattering decays also exhibited two rate constants. However, since the first rate constant corresponded to only a portion of the amplitude signal, which decreased with increasing [ATP], the inventors could obtain representative data for $K_{+5}$ at higher concentrations of ATP (>2.5 mM). At those ATP concentrations, values of $K_{+5}$ were very approximated between mutant and wt Sm HMMs. Thus, the inventors concluded that the G343S substitution in SmM altered the nucleotide-binding constants of the molecule without changing its nucleotide-release properties.

To better understand the mechanisms underlying these effects the inventors examined the structural impact of the G343S (Sm; 342 ChSkM) mutation using the atomic coordinates of the gizzard SmM myosin (Dominguez et al., 1998). This analysis yielded two important observations. First, G343 is in a "generously" allowed region of the Ramachandran plot; in other 3D myosin structures such as the ChSK, G342 is disallowed (see below). This is relevant because while Gly could be anywhere in the Ramachandran plot, all other residues including Ser would introduce significant steric constraints to the region. Importantly, G343 (G342 ChSK) is located on a tight turn connecting two differently oriented α-helices that undergo structural transition from the acto-myosin ADP state to the rigor state (Volkmann et al., 2000). Thus, if G342 works as a pliable hinge, movements of the connecting helices could be severely hindered by the side chain of Ser. Replacement of G342 by a polar residue like Ser also adds the possibility of polar interactions, namely H-bonds. In fact, when replacing Gly by Ser in its most predominant rotamer, the inventors observed the presence of a highly conserved Arg (R445 Sm, R444 in ChSK and K436 in Dicty) within H-bonding distance to Ser but not to Gly (FIG. 6A-B). This second important observation indicates that the highly probable H-bond between S343 and R445 in the Sm mutant should introduce increased rigidity to the region. Importantly, R445 is located in the helix lining the upper 50 KDa sub-domain of the actin-binding cleft and in close proximity to switch-1 and P-loop. Recent low-resolution structures indicated that closure of the 50 KDa cleft in the rigor state and its subsequent re-opening upon ATP binding (Bauer et al., 2000) are both mediated by mass movements of the upper 50

KDa sub-domain (Volksman et al., 2000). In this context, it is probable that the H-bond between S343 and R445 could affect the ATP-induced conformational transition(s) leading to acto-HMM dissociation, detected in our kinetic analysis of the mutant.

Estimating the impact of G342S on the mouse α myosin. One puzzling observation of this study was that the G342S mutation produced different effects in different myosins. In SmM myosin (HMM), the G343S substitution altered $K_1 \cdot K_{+2}$ without changing $K_{+5}$, whereas in mouse-α the same substitution appears to affect predominantly $K_{+5}$ (note that estimated $K_{max}$ values for $K_1 \cdot K_{+2}$ were not rate-limiting in either rat-α or mouse-α myosins). So, although G342S substitution changes the nucleotide turnover properties of both myosins, it affects nucleotide-binding in SmM and nucleotide-release in mouse α myosin.

Characterizations of the structural impact caused by the G342S mutation in the mouse-α myosin backbone and its role in modulating ADP release are difficult to perform for two main reasons. First, 3D structures of mammalian cardiac myosins are yet to be produced. Second, the coordinates of the two recent low-resolution acto-myosin structures representative of the ADP and rigor states (Volkmann et al., 2000) are not available. Despite the limitations, the impact of the G342S substitution in the mouse-α myosin can be at least partly inferred from the existing 3D structures of myosins, because all of them (and also presumably the mouse-α) report high structural conservation in the vicinity of G342 irrespective of the degree of sequence divergence. Likewise, the inventors found that R444 (ChSkM) is also conserved among myosins II. Thus, they examined the likelihood of these residues participating in establishing an H-bond in the various myosin structures.

The distances between the Oγ atom of the mutated Ser and NH* side-chain atoms of Arg in various myosin structures are listed in Table 1. In Dicty, R444 is K436 and exhibits variable distances of the Nz atom to the Oγ atom of Ser, depending on the structure. Although the side-chains of Lys adopt different conformations in various Dicty structures, most of them exhibit high thermal motion parameters (B-factors), imlying the existance of flexibility within the crystal structures. This suggests that replacement of Gly by Ser could cause small adjustments of the side chains to allow formation of the H-bond, which would effectively stabilize this region of the protein.

TABLE 1

Distances between S342 Oγ and NH* side chain atoms of R444 in several 3D atomic structures of myosins. Note that residue 342 (ChSK numbering) is Gly in all of the structures and that side chain S342 was superposed in the Cα of all structures.
Data schematization:

| Source | PDB code (state) | Distance (A) SOγ - N* R/K | Distance (A) |
|---|---|---|---|
| ChSk | 2mys (II) | 3.9, 4.4 (2.8, 3.7)# | S342 Oγ - NE2 Q448 1.2 (2.7)# |
| ChSm | 1br1 (I) | 2.5 | |
| | 1br2 | 2.4, 2.9 | |
| | 1br4 | 3.4 | |
| Dict. | 1 vom (II) | 6.5 | |
| | 1mnd | 3.1 | |
| | 1mmd (I) | 4.4 | |
| | 1fmv | 4.4 | |
| Scal. | 1b7t (III) | 3.9, 3.7 | | after structural adjustement to avoid atomic clash or to optimize H-bond

The impact of the G342S substitution on the backbone structure of ChSkM was particularly important because among existing 3D structures, ChSK is the one most closely related to the cardiac myosins (>90% homology). Here, replacement of G342 by Ser (FIG. 7A) produced an additional observation not seen in the structures previously analyzed—the Oγ atom of S342 is only 1.2 A away from the Nε2 of Q448. A side-chain adjustment was therefore necessary in the inventors' analysis to avoid atomic clashes (FIG. 7B). Importantly, the inventors observed that Gly 342 is disallowed in the Ramachandran plot for the ChSK structure. This indicates that in order to accommodate a Ser residue, the side-chain positions in the mouse-α myosin backbone must be invariably different from what the inventors observe in the ChSK 3D structure. Remarkably, following the side chain adjustments (Table 1), they found that the proximity of the Nε2 of Q448 to the Oγ atom of S342 supports the formation of a second H-bond between these two residues. In addition, depending on the side chain position, the NH* atom of R444 could become conspicuously close (within H-bond distance) to the side chain oxygens of both Q448 and S342. Importantly, these interactions are not possible in SmM myosin (and Dicty) because Q448 is replaced by a non-polar residue (Ala in Sm; Val in Dicty). However, in cardiac myosins, Q448 is replaced by Thr (another polar residue). Since Q448 is also Thr (T445) in scallop myosin, we used the scallop structures to examine the possible role of this residue in establishing polar interactions. Indeed, the inventors found that the OG1 atom of T445 in scallop myosin (Q448 ChSK) is at 2.7 A distance from the OG of G339S (342 ChSkM) and in close proximity to the NH1 atom of the conserved R441 (R444; ChSkM). Furthermore, the distance between the Cα of T445 and G339 (G342 ChSkM) is maintained in the 3 scallop structures representative of different ATP states (1b7t-III, 1dfk-I and 1df1-III; the last two only poli-alanine model is available), pointing towards conservation of the H-bond. In view of this, the inventors performed one final analysis by double replacing G343S and A449T in the SmM backbone to better predict the eventual structural differences compared to the mouse-α myosin. The results indicated that the distance between the side-chains of S343 and T449 (Sm) was 3.3 A, confirming that the presence of Thr in that position could in fact establish an H-bond with S343 (S342 ChSkM). Since this region of the molecule is structurally conserved in all 3D structures, it appears that the functional impact of the G342S mutation in any given myosin, including mouse α, will largely depend on the presence of polar residues within H-bonding distance.

Although little is still known regarding the conformations of myosin while bound to actin significant advances were made by recent computer based-fitting studies of crystal structures into three dimensional reconstructions obtained by electron cryomicroscopy and by mapping of structural and dynamic changes in the acto-myosin complex (Volkmann et al., 2000). From that study it appears that the structural transitions associated with nucleotide-binding and nucleotide-release are related to opening or closing of the 50 KDa cleft (Volkmann et al., 2000).

In this study, the inventors demonstrated that R444 and Q448 in ChSkM (R444 and T448 in mouse α myosin) are located in the α-helix lining the upper 50 kDa cleft and both appear to be well positioned to establish H-bonds with S342 (ChSkM) (and possibly with one other). Thus, both would be in position to affect the conformational transitions associated with nucleotide turnover. Since only one of these H-bonds is possible in SmM, these differences could be explain the differing effects due to the G342S mutation in SmM myosin and in mouse α myosin.

The inventors' observations regarding the role of the G342S mutation highlight the importance of this myosin region upon regulation of nucleotide turnover kinetics. So far in this discussion, the inventors have provided strong evidence in support of the notion that kinetic changes introduced by the G342S mutation are probably linked to increased rigidity in this otherwise flexible region. However, it must be emphasized that the steric constraints introduced by the side chain of S342 could have far reaching effects beyond those highlighted in this discussion.

G342 connects two differently oriented helices. One of these helices, shown in FIGS. 6 and 7 (helix colored red 324-340 ChSK) has been shown to constitute an interaction site for loop 1 in both ADP-bound and rigor states (Volkmann et al., 2000). Loop 1 has long been implicated as a determinant of nucleotide turnover kinetics in myosin (Spudich, 1994). While changes in loop 1 sequence have been shown to affect the rate of ADP dissociation in SmM myosin (Kelley et al., 1993; Rovner et al., 1997) its near ablation almost abolished $K_{+5}$ (Sweeney et al., 1998). Recently, the inventors showed that near ablation of the loop 1 also alters the nucleotide-binding properties of the gizzard SmM myosin, speeding up $K_1 \cdot k_{+2}$. Thus, loop 1 plays an important regulatory role in nucleotide turnover. In cardiac myosins the sequence of loop 1 is identical among MHC subunits of the β and α isoforms, respectively, and so, the inventors have previously suggested that the role of the loop in tuning nucleotide turnover kinetics in cardiac myosins would depend upon the sequence composition of the interaction site (Sant'Ana Pereira et al., 2001a). The sequence composition of the two helices connected by G342 is highly variable among cardiac myosins. Furthermore, some of the residues in the two helices are involved in interactions with each other, namely, a salt-bridge involving a negatively charged residue (R348 and E336 in ChSkM) thought to provide one of the possible binding-sites for positively charged Lys residues of loop 1 (Volkmann et al., 2000). Since the region encompassing the two helices (and G342) undergoes structural transitions from the ADP-bound to the rigor state and from the rigor state to the ATP-bound state (i.e., bound to loop 1 in the first two force generating states but disordered in the ATP dissociating state (Rayment et al., 1993a; Bauer et al., 2000)), the loop could function as a "latch" facilitating structural transitions associated with nucleotide binding and release. Interestingly, in the low-resolution structures published by Volkmann and co-workers (2000), loop 1 and its interactive α-helix appear to rotate away from the helix of the upper 50 KDa sub-domain which moves inwards, in the opposite direction, to further close the cleft in the rigor state (see their FIGS. 4A and 4B). Since ADP release occurs in this structural transition, the concerted role of loop 1 with its connecting α-helix along with the helix lining the upper 50 KDa cleft may constitute intricate elements of a true nucleotide binding and dissociation domain. Here, interactions between residues R444 and T408 (ChSkM numbering) of the 50 kDa helix with the side chain of S342 (H-bonds) could greatly affect these mechanisms. Loop 1 sequences of gizzard SmM myosin and mouse α myosin differ greatly in size, a factor previously shown to modulate loop 1 regulation of nucleotide turnover (Rovner et al., 1997; Sweeney et al., 1998). Since the steric constrains caused by the introduction of the Ser side chain could affect the interaction/conformational transitions of loop 1 binding to the 324-340 α-helix, different loop sizes could produce different effects. Surely, a much shorter loop as in mouse-α myosin would be more susceptible to small perturbations. This factor could also contribute to the different effects on nucleotide kinetics due to the G342S mutation in SmM and mouse α myosin.

The main objective of the present invention is to provide a mouse-α myosin template representative of other myocardial myosins, including the human. Mouse transgenic models are overwhelmingly regarded as effective tools to access human myocardial function and disease. In this study, the inventors provide strong evidence that the G342S substitution in mouse-α myosin is functionally significant and may confer unique kinetic properties to this isoform. Although the conclusions reached in this study need to be confirmed by reversal of the S342G in the mouse-α backbone, the inventors' analyses predict structural and functional impacts for this substitution in all backbone structure of myosins II analyzed. In addition, the inventors speculate that this substitution may have far reaching effects in myosin function in that it may affect the regulatory role of loop 1. Since the inventors' comparative analysis between mouse-α and rat-α provide a model of minimal sequence divergence in which the only varying residue in what the inventors designate "dissociation domain" is G342, the validity of this contention can be further demonstrated by examining the role of swapping loop 1 sequences in mouse background comprising either G342 or S342. According to their analysis, the inventors anticipate that changes in loop 1 sequences, providing that they do not display dramatic changes in length, may tune nucleotide turnover in presence of G342 but not of S342.

EXAMPLE II

Substitution of Loop 1 and/or IMD of MOUSE α-Cardiac Myosin to Yield Mutants with Unique Kinetic Properties A. Introduction Several studies (reviewed in 54) indicate that there are at least 7 and possibly 10 isoforms of myosin heavy chains (MHC) expressed in mammalian striated muscle cells: cardiac α and β MHC's, skeletal slow (type 1, equivalent to cardiac β MHC), embryonic, neonatal and three fast (types 2a, 2b, 2x) MHC's, and possibly a skeletal superfast MHC. There is remarkable conservation of MHC isoforms among vertebrate species, although the primary sequences of analogous MHC's may differ. Since mechanical properties of muscle are likely to be determined at least in part by its mix of myosin heavy chains, the potential expression of 7 different MHC's in skeletal muscle and 4 in cardiac muscle provides a considerable range of adaptive responses to the work demanded of each muscle. The inventors' recent work suggests clearly that even in the case of muscles expressing a given MHC, e.g., cardiac β MHC, there are differences in function between species, most likely due to small variations in primary sequence. The maximum velocity of shortening ($V_{max}$) of rat myocardium expressing mainly β MHC is substantially greater than $V_{max}$ in pig or human myocardium expressing the same isoform.

Myosins in striated muscles also differ in light chain (MLC) content (54). There are two MLC's bound to each MHC, i.e., the regulatory light chain (RLC; also called $LC_2$ or P-light chain) and the essential light chain (ELC). Previous studies have shown that extraction of RLC alters $V_{max}$ and the kinetics of tension development in adult fast-twitch fibers (14,23), and transgenic expression of ventricular RLC in mouse atria was found to increase mechanical $V_{max}$ (7,49). Varied expression of ELC isoforms has also been associated with variations in dynamic mechanical properties (6,42,63,64), and the ELC's must be present to achieve maximum sliding velocities (32) and force (71) in in vitro assay systems. While changes in $V_{max}$ due to altered MLC content are generally not as large as those for altered MHC (6), variations in MLC's provide another avenue for adaptation of muscle to chronically altered work loads.

Myosin in adult mammalian ventricles is expressed as one of three native isoforms based on MHC content (31): $V_1$ contains two α MHC's, $V_2$ contains one α and one β MHC, and $V_3$ contains two β MHC's. Adult rabbit ventricular myosin is ~85% $V_3$ and 15% $V_1$ and adult rat ventricular myosin is almost entirely $V_1$, but the proportions of each isoform vary depending on developmental stage—$V_3$ is the predominant fetal isoform in all mammals, and expression of $V_1$ begins around the time of birth. In neonatal rabbits, $V_1$ increases to >50% by ~2 wks of age and then gradually decreases to adult levels. Cardiac MHC content also varies widely in disease and under a range of experimental conditions (39). For example, right ventricular hypertrophy due to sudden pressure overload induces expression of $V_3$ in rabbits (43) and rats (36). Thyroid status also modulates expression of cardiac MHC's: α MHC expression is completely downregulated in hypothyroidism in rabbits (31) and rats, and is up-regulated by hyperthyroidism (10).

$V_{max}$ has been related to the MHC content of myocardium—expression of $V_3$ reduces $V_{max}$, slows cross-bridge cycling rate, reduces ATPase activity, and increases the efficiency of contraction (1,67). $V_3$ also slows the rate of tension recovery following a sudden release (4) or a sudden increase in $Ca^{2+}$ concentration and slows relaxation. Expression of $V_1$ has effects that are opposite these.

The intrinsic work rate (power) of myocardium is perhaps its most important characteristic, since power must be well matched to the load borne by the muscle. Typically, faster muscles in terms of $V_{max}$ and ATPase rate are capable of developing much greater power and therefore have faster work rates than slower muscles moving an identical load (74). However, muscles that are very fast such as sonic muscles (involved in sound production) generate speed at the expense of power development. Such also appears to be the case in mouse cardiac muscle in which the kinetics of the myosin motor are tuned for speed at the expense of power. To understand the molecular basis of power generating characteristics of a muscle, as well as the kinetics of myosin turnover, it is initially most appropriate to study the MHC, since this is likely to be the most important single determinant of $V_{max}$ in striated muscles (6).

The structural features of the MHC molecule that determine the kinetics of ATPase activity are not yet understood (18,50,69), although the high-resolution crystal structure of chicken pectoralis myosin has provided a baseline of important information for initiating mechanistic studies (51). In this aspect of the invention, the nucleotide binding pocket and flexible loop 1 adjacent to the pocket are utilized as regions that are critical regulators of ATPase activity. Two caveats must be set forth: (i) loop 1 is flexible and its structure is indeterminate in x-ray studies (51), and (ii) it is unlikely that loop 1 is the only regulator of turnover kinetics. Also, while it is generally accepted that mechanical $V_{max}$ and actin-activated myosin ATPase activity are proportionate variables (3), this is not always the case (70), suggesting that chemomechanical transduction involves more than a single mechanism. For example, in one series of experiments Spudich, et al. (68) replaced residues within loop 2 actin binding loop) of *Dictyostelium* MHC with amino acids characteristic of rabbit fast skeletal myosin. While the chimera exhibited increased ATPase activity, there were no changes in in vitro thin filament sliding velocity. Based on these and other results, it was suggested that hypervariable loop 2 might regulate actin-activated myosin ATPase activity (68) while loop 1 (near the ATPase site, or nucleotide binding pocket) determines $V_{max}$ by tuning the rate of ADP release from myosin (59,69).

The inventors' focus on loop 1 and the binding pocket as key elements in regulating rates of nucleotide turnover in myosin is stimulated by recent experimental results. Perhaps most important is the finding that loop size is a significant factor in myosin turnover kinetics. For example, in smooth muscle myosins, there are two variants of loop 1 (also called the ATPase loop) which are products of an alternatively spliced gene—in phasic smooth muscle the loop contains 7 amino acids (QGPSFSY) more than the comparable loop from tonic smooth muscles (29). The first study examining the consequences of this loop variation showed that gizzard myosin containing the 7 amino acid insert had twice the ATPase activity of aortic myosin which does not have the insert, and also moved thin filaments 2.5-fold faster in an in vitro motility assay (29). These studies were later extended by removal of the insert, which was found to halve both ATPase activity and sliding velocity (52). These kinetic effects of the insert were found to be due to a change in the rate of ADP release, which was 3 times faster in gizzard acto-S1 than in myosins without the insert (65). Sweeney, et al. (65) found that the size of loop 1 is a significant determinant of ATPase activity and in vitro sliding velocity. As loop size was increased, sliding velocity and the rate of ADP release both increased although not in strict proportion. In fact, insertion of loops from various type II myosins resulted in sliding velocities that did not strictly correspond to the sliding velocities of native myosins, indicating that there are other important determinants of myosin turnover kinetics. Together, these results partially confirm the hypotheses proposed earlier by Spudich (59), i.e., the ATPase loop (loop 1) appears to control the rate of ADP release and thus the motility of the motor protein; however, in all of these experiments the actin binding loop (loop 2) was identical, so that regulation of ATPase activity is certainly not restricted to loop 2, if it is involved at all.

The inventors' results support the concept that loop 1 regulates the kinetics of ADP release. The inventors' antibody to a loop 1 peptide caused a 2 to 3-fold increase in maximum tension and 40% reduction in $V_{max}$, which is consistent with reduced rates of ADP release from the A.M.ADP complex. While results such as these are striking, they cannot be interpreted to mean that loop 1 is the only determinant of nucleotide turnover kinetics. The idea that other regions of the myosin molecule have roles is a logical conclusion from examination of sequence data from type II myosin isoforms that exhibit distinct kinetic properties. Among cardiac myosins, β MHC's exhibit significantly slower sliding velocities than α MHC's, and yet loop 1 in β MHC is just 1 amino acid shorter than the loop in α MHC. Further, there is a highly conserved charged motif ($^{204}$DRSKKD$^{209}$) within cardiac MHC's regardless of isoform or species source. Loop 1 is the same size in all skeletal fast MHC's, and there is also a highly conserved motif within the loop ($^{204}$E/DKKKEE$^{209}$), and yet $V_{max}$ varies considerably among fast isoforms, i.e., 2b>2x>2a (54). Finally, there is a 3-fold difference in $V_{max}$ in rat and pig muscle cells expressing β MHC, and yet, their loop 1 sequences are identical, implying that other factors contribute to the regulation of kinetics.

The presence of highly charged consensus motifs specific to cardiac MHC's suggests the possibility that these motifs are involved in electrostatic interactions between loop 1 and other parts of the myosin molecule. The inventors hypothesize that such interactions modulate the flexibility of loop 1 and thereby alter loop 1 regulation of nucleotide turnover in the binding pocket. A mechanism such as this could account for relatively large kinetic effects of small numbers of amino acid substitutions in loop 1 (e.g., at residue 210 in skeletal fast myosins), if the substitutions had steric effects within the loop or within the region of interaction. From their examinations of the crystal structure of myosin, the inventors have identified the "interactive micro-domain", or IMD (residues 323-351) as the most likely site of interaction with loop 1. While not wishing to be held to only one theory of operation, the following sets forth specific elements of a working model for regulation of the kinetics of ADP release from myosin (and therefore of $V_{max}$ and power generation):

1. Loop 1 regulates ADP release kinetics, which is based on findings that loop size (and flexibility) is an important determinant of myosin turnover kinetics (29,52,65), removal of the loop slows and equalizes the rate of ADP release from different isoforms of skeletal and cardiac MHC's (65), and the inventors' own finding that antibodies to loop 1 peptide increase force and slow $V_{max}$ in skinned fibers.

2. Loop 1 is not the only regulator of kinetics, since mechanical $V_{max}$ of rat β MHC is 3-fold greater than $V_{max}$ of pig β MHC despite the fact that loop 1 is identical in the two isoforms.

3. Loop 1, which is electropositive, interacts with the helical portion (323-340) of the IMD, which is electronegative, thereby triggering ADP release from the nucleotide binding pocket.

4. In myosin in the absence of actin, loop 1 interaction with the IMD is unlikely or reduced, but once nucleotide-bound myosin binds to actin, there is a conformational change in the portion of the myosin head distal to the nucleotide binding pocket, which increases the likelihood of interaction. While these conformational changes have not been observed in crystal structures to date, Rayment has inferred that they occur (and may require actin to be bound) since the nucleotide binding pocket accommodates a penta-phosphate nucleotide analog.

5. The inventors propose that isoform-specific kinetic properties of cardiac MHC's involve specific mechanisms which influence the extent and rate of loop 1/IMD interaction: (a) Loop 1 of α MHC is longer by one residue than loop 1 of β MHC, which according to results from Sweeney (65) in smooth muscle myosin could contribute to the faster turnover kinetics of α MHC; and (2) the inventors are further aware of specific amino acid substitutions at residues 328, 331, 336, 345 and 351 of the IMM in β MHC's. Depending on the residues that are present, e.g., pro 345 in rat β MHC vs ser in pig, the conformation of the IMD will change and affect the likelihood of its interaction with loop 1.

6. Electrostatic interactions between residue 348 in the IMD and the helical portion of the IMD are important for transmitting the actin-induced conformational change from the distal portion of the myosin head through the IMD, which in turn facilitates interaction of loop 1 with the IMD. In this context, the inventors suggest that residue 345 plays an important role in modulating the interaction of lys348 with the helical portion of IMD, i.e., there is a proline at 345 in rat β MHC and serine in porcine β MHC and much greater $V_{max}$ in rat β MHC.

B. Isoform-Specific Kinetic Properties of Cardiac MHCs.

With Leiden and Solaro (15), the inventors studied mechanical measurements on skinned cardiac myocytes. Myocytes from normal mice and from transgenics expressing slow skeletal troponin I (ssTnI) under control of a cardiac-specific promoter. This was done to assess the roles of PKA-dependent phosphorylation of TnI in myocardial contraction. The attachments to the apparatus had low compliance since sarcomere length and uniformity were maintained when myocytes were transferred from relaxing solution to maximally activating solution (lower panel). The $Ca^{2+}$ sensitivity of tension was significantly greater in ssTnI transgenic myocytes ($pCa_{50}$ 5.98±0.04) than in wild-type ($pCa_{50}$ 5.61±0.03). When wild-type myocytes were treated with protein kinase A (PKA), the tension-pCa relationship shifted to higher $[Ca^{2+}]$ ($pCa_{50}$ 5.42±0.03), i.e., $Ca^{2+}$ sensitivity of tension was reduced. However, PKA had no effect on $Ca^{2+}$ sensitivity in ssTnI myocytes ($pCa_{50}$ 5.97±0.03). This result supports the concept that phosphorylation sites on cardiac TnI mediate the PKA-induced decrease in $Ca^{2+}$ sensitivity of tension in myocardium. The inventors also used the slack-test method to assess $V_{max}$ in wild-type and ssTnI myocytes at pCa 4.5. Under control conditions, $V_{max}$ was similar (wild-type 2.26±0.14 muscle-lengths/s; ssTnI 2.56±0.20 ML/s); however, treatment with PKA increased $V_{max}$ in wild-type (3.64±0.24 ML/s) but not ssTnI myocytes (2.60±0.23 ML/s). Thus, phosphorylation of cardiac TnI mediates the increase in mechanical $V_{max}$ reported previously in PKA-treated myocytes (47) and modulates crossbridge cycling kinetics.

The inventors have also examined force-velocity and power-load relationships in skinned myocytes from rat hearts. The inventors have exploited their methodologic advances to study the activation-dependence of force-velocity and power-load relationships in single skinned cardiac myocytes (35). Records of shortening under load in both living and skinned preparations of cardiac muscle have been reported to be curvilinear, i.e., continually slowing as shortening proceeds, possibly due to passive elasticity in parallel or in series with active elements or due to shortening-induced inactivation of cycling cross-bridges. To investigate the basis for this phenomenon, the inventors assessed shortening in rat skinned ventricular myocytes, which were tied into the apparatus using stainless steel troughs. Resting sarcomere length was adjusted to ~2.30 μm, which yielded a mean cell length of 167±24 μm and mean cell width of 22.8±3.2 μm. Maximum tension at 12° C. was 20.4±8.8 kN/mm² at a sarcomere length of 2.33±0.11 μm. Shortening velocities were measured over a range of loads using an electronic servo system (66), which yielded hyperbolic force-velocity relationships and mean $V_{max}$ of 2.28±0.95 muscle lengths/sec. Unlike previous reports, length traces during isotonic shortening were linear during maximal activation, most likely due to the low compliance of attachments to the cell ends. The inventors' findings suggest that curvilinear shortening in multicellular preparations is due to progressive compression of connective tissue or is an artifact of the preparations, e.g., compliant connections to the apparatus.

The inventors next made a targeting construct as a first step in producing a transgenic α $MHC^{βloop}$ mouse to examine loop 1/IMD interactions.

Cloning the mouse α MHC gene. DNA pools from a mouse strain SV129 BAC library (Genome Systems) were screened by PCR using a primer pair that amplified exon 12 of the mouse cardiac α MHC gene. One BAC clone containing the mouse cardiac a-MHC gene was identified, and obtained from Genome Systems. DNA was prepared and a 23 kb Hind III fragment and a 4.4 Eco RI fragment that hybridized to the exon 12 probe were sub-cloned into the vector pBluescript KS+ (Stratagene).

Mutagenizing the mouse α MHC loop 1 was carried out as follows. DNA sequence analysis of the 4.4 kb Eco RI fragment containing plasmid (pMHC-R4.4) allowed the localization of exons 7 and 8 to a 1.4 kb Eco RI-Eco RV fragment which was sub-cloned into pBluescript KS+ (Stratagene) and used in a whole plasmid synthesis site-directed mutagenesis (73).

Following is a comparison of the loop 1 regions of the mouse cardiac α MHC cDNA (SEQ ID NO:3) and the corresponding amino acid sequence (SEQ ID NO:4) and the rat/pig β MHC cDNA (SEQ ID NO:5) and the corresponding amino acid sequence (SEQ ID NO:6):

```
mouse αMHC
694 att gca gcc ata ggg gac cgt agc aag aag gaa aat cct aat gca aac aag ggc acc ctg gag g 757
(SEQ ID NO:3)
198 I   A   A   I   G   D   R   S   K   K   E   N   P   N   A   N   K   G   T   L   E   -
(SEQ ID NO:4)

pig βMHC
602 att gct gcc att ggg gac cgc agc aag aag gac cag acc c-- -ca ggc aag ggc acc ttg gaa g 662
(SEQ ID NO:5)
198 I   A   A   I   G   D   R   S   K   K   D   Q   T       P   G   K   G   T   L   E   -
(SEQ ID NO:6)
```

Oligonucleotide primers that allow substitution of the rat/pig β MHC loop 1 for the mouse cardiac α MHC loop 1 in the α MHC gene were synthesized (SEQ ID NQ:7). Capitalized nucleotides represent the exon 7 sequence; lower case letters represent intronic sequence. Translationally silent nucleotide substitutions (bolded in the DNA sequence shown below) allowed the introduction of a novel Pvu I restriction site.

```
                    P
                    v
                    u
                    I                        β loop 3' primer (5' to 3')
GCATTGCAGCCATAGGCGATCGTAGCAAGAAGGACCAGACCCCAGGCAAGgtgagtgtgggtcataggct
---------+---------+---------+---------+---------+---------+---------
CGTAACGTCGGTATCCGCTAGCATCGTTCTTCCTGGTCTGGGGTCCGTTCcactcacacccagtatccga
    β loop 5' primer (3' to 5')
     I  A  A  I  G  D  R  S  K  K  D  Q  T  P  G  K
```

These primers were used in a whole plasmid synthesis (WHOPS) site-directed mutagenesis (73). The PCR reaction contained 50 ng of pMHC-RV1.4 template DNA, 0.2 mM of each phosphorylated primer, 250 mM dNTPs, 1×PFU buffer and 2.5 U PFU polymerase (Promega) in a final volume of 50 μl. The cycling conditions were: 2 min at 95° C., 30 cycles of 45 s at 95° C., 17 min at 72° C., followed by 35 min at 72° C. 10 μl of the PCR reaction was run on an agarose gel to check the formation of the appropriately sized PCR product. 20 U of Dpn I and 2.5 U of PFU polymerase (Promega) were added directly to the remainder of the PCR reaction and incubated at 37° C. for 2 h, followed by a 30 min incubation at 72° C. ATP to a final concentration of 1 mM and 3 U DNA ligase were added to 15 μl of this reaction and incubated overnight at 16° C. 0.5 μl of the ligation was transformed into electrocompetent XL1Blue cells (Stratagene). Plasmid DNA was prepared from several of the resulting colonies and digested with Pvu I to identify mutagenized clones. DNA sequence analysis of one of these clones demonstrated the presence of the translationally silent Pvu I site and the substitution of the rat/pig β MHC loop 1 sequence for the mouse α MHC loop 1.

In order to further examine loop 1/IMD interactions, the inventors made a rat α MHC/pig β loop knock-in vector for use in subsequent transgenic animal production. A cassette containing the PGK-neo gene and the HSV-thymidine kinase gene flanked by two loxP sites was inserted into intron 9 as a selectable marker.

Transformed mouse ES cells that integrate the PGK-neo/TK cassette may be selected by growth on G418. Neo$^r$ cells may be selected, replicated and expanded. DNA isolated from Neo$^r$ ES clones may be digested with restriction enzymes that will allow selection of the insertion by homologous recombination, transferred to a charged nylon membrane by Southern blotting, and hybridized to radio-labeled DNA probes that lie outside the region included in the targeting vector. Correctly targeted ES clones that contain the pig/rat β MHC loop 1 substitution are subsequently expanded and micro-injected into C57B1/6 blastocysts according to standard techniques. Chimeric mice may be mated to C57B1/6 partners and the resulting agouti pups analyzed by Southern blot for the presence of the knock-in chromosome. The PGK-neo/TK cassette may be "floxed" or removed with Cre recombinase-mediated recombination by crossing heterozygous knock-in mice with mice the express Cre recombinase in the male germline under the control of the protamine promoter (46). Cre-recombinase mediated recombination will occur in spermatocytes and the recombined alleles will be incorporated into the fertilized egg. PCR and Southern blotting may be used to identify mice carrying the floxed knock-in allele. Adult mice homozygous for the β-MHC loop 1 substitution will thusly be available for kinetic analyses. The production of transgenic animals was discussed previously and is known in the art (e.g., 20,27).

The inventors have also performed a comparison of loop 1 sequences in myosin heavy chain isoforms. Given the putative role of loop 1 in determining kinetic properties of myosin, the inventors studied the loop in various myosins as an important step in investigating whether sequence variations might account for the differing characteristics of these isoforms. The inventors have cloned and sequenced the part of the MHC gene that encodes this domain in isoforms from various species. Sequences corresponding to loop 1 in various MHC isoforms, aligned according to the chicken pectoralis numbering of Rayment, et al. (51). The sequences of human 2a, pig 2a, human 2x, rabbit 2x, rabbit 2b, pig β cardiac and rabbit β cardiac and were obtained in our laboratory as predictions from cDNA's generated by RT-PCR/cloning of electrophoretically characterized myocytes (53) and subsequent sequencing. The rest are gene bank sequences. The following conclusions may reasonably be drawn from these comparisons:

(1) loop 1 of the β-cardiac MHC is shorter by 1 amino acid than that of α-cardiac MHC and is shorter by 2 amino acids than loop 1 of the skeletal type II isoforms;

(2) for a given MHC isoform, loop size is identical irrespective of animal species, i.e., loop size is the same in all β-cardiac MHC's, loop size is the same in all α-cardiac MHC's, and loop size is the same in all skeletal mammalian MHC isoforms;

(3) all cardiac MHC's have a highly conserved motif ($^{204}$DRSKKD/E$^{209}$) in loop 1 irrespective of isoform or animal species, and all skeletal muscle MHC isoforms have an equally conserved motif ($^{204}$E/DKKKEE$^{209}$) which differs from that in cardiac MHC's; and (4) among skeletal MHC isoforms the amino acid substitutions in loop 1 are confined to residues 210 and 212; among cardiac α and β MHC isoforms, the amino acid sequence of loop 1 is identical for all but the human isoforms, which exhibit a 211 T/S substitution in β MHC and a 211 P/A substitution in α MHC.

The inventors have observed mechanical effects of antibodies to loop 1 of skeletal 2x myosin. To test whether loop 1 plays a role in regulating the kinetics of myosin from mammalian striated muscles, the inventors raised polyclonal antibodies against a synthetic peptide equivalent to the $^{203}$DKKKEEATS$^{212}$ sequence of rabbit 2x MHC and applied the antibodies to relaxed skinned fibers from rabbit psoas muscle, which is mainly 2x MHC. The inventors hypothesized that if loop 1 influences the kinetics of nucleotide dissociation, antibody binding to the loop would slow these kinetics and thereby increase force and slow muscle shortening. Consistent with this idea, the inventors observed a dramatic 2 to 3-fold increase in maximum $Ca^{2+}$-activated force due to infusion of antibody, an effect the inventors were unable to reverse with extensive washing in relaxing solution, and a 40% reduction in $V_{max}$. These results are important for two reasons. First, the results are consistent with the interpretation that antibody binding caused ADP to be held in the nucleotide binding pocket for an extended period, slowing the rate of cross-bridge detachment and increasing the total number of cross-bridges in force generating states. Second, the potentiation of force suggests that under normal conditions (no antibody) the maximum force generated by a muscle involves 40% or fewer of the total myosin heads in the fiber.

The inventors also treated skinned type 2x skeletal muscle fibers with the peptide to which the antibody was raised: peptide was infused while the fibers were relaxed but there were no effects on force during maximal activations. This result might be taken as evidence against our primary hypothesis concerning possible roles of loop 1 in myosin function. However, a likely interpretation is that the binding of the peptide is sterically constrained so that binding occurs only when myosin or the myosin-actin complex is in a particular transitional state that does not occur or is sparsely populated in relaxed skinned fibers.

The inventors further measured turnover kinetics of cardiac β MHC from human and hypothyroid rat (loop 1 is identical in human and rat β MHC, but IMD differs significantly) using a range of functional assays. In one set of experiments, the inventors used the slack test to measure

| SKELETAL MHC ISOFORMS | | | | | | | | | | | | | | |
|---|---|---|---|---|---|---|---|---|---|---|---|---|---|---|
| | 204 | | | | | | | | | | | 216 | | |
| chick pect | E K | K K E E | Q | - | S | G | K M | Q | G T L E | D | (SEQ ID NO:8) |
| human/pig 2a | E K | K K E E | P | T | S | G | K M | Q | G T L E | D | (SEQ ID NO:9) |
| human 2x | E K | K K E E | V | T | S | G | K M | Q | G T L E | D | (SEQ ID NO:10) |
| rabbit 2x | D K | K K E E | A | T | S | G | K M | Q | G T L E | D | (SEQ ID NO:11) |
| rabbit 2b | D K | K K E E | P | T | P | G | K M | Q | G T L E | D | (SEQ ID NO:12) |

| CARDIAC MHC ISOFORMS | | | | | | | | | | | |
|---|---|---|---|---|---|---|---|---|---|---|---|
| human α | D R | S K K D | N | A N A | - | N | K G T L E | D | (SEQ ID NO:13) |
| rat α | D R | S K K D | N | P N A | - | N | K G T L E | D | (SEQ ID NO:14) |
| mouse α | D R | S K K E | N | P N A | - | N | K G T L E | D | (SEQ ID NO:15) |
| human β | D R | S K K D | Q | S P G | - | - | K G T L E | D | (SEQ ID NO:16) |
| pig β | D R | S K K D | Q | T P G | - | - | K G T L E | D | (SEQ ID NO:17) |
| rat β | D R | S K K D | Q | T P G | - | - | K G T L E | D | (SEQ ID NO:18) |

$V_{max}$ of rat and human type I skeletal muscle fibers, both of which express the β MHC. At 15° C., maximally $Ca^{2+}$-activated type I fibers from rat are ~3-fold faster (0.96±0.2 muscle lengths (ML)/s; n=21) than human type I fibers (0.35±0.35 ML/s, n=15). Similar results were obtained in single cardiac myocytes from pig and rat expressing exclusively the β MHC isoform, determined by ultra-sensitive SDS-PAGE (expression of β-cardiac MHC in rat was induced by thyroidectomy). Further studies showed that the actin-activated ATPase activity of rat β MHC was substantially greater than for pig β MHC (1.75 $s^{-1}$ vs 0.76 $s^{-1}$). The inventors measured a mean actin sliding velocity of 0.86 $\mu m \cdot s^{-1}$ (30° C.) using preparations of HMM from pig β MHC. The inventors have also used stopped-flow techniques to assess the effects of ADP on ATP-mediated dissociation of acto-HMM (56) and found that the maximum rate constant for dissociation of acto-β $HMM_{pig}$ was ~35 $s^{-1}$, which the maximum for acto-β $HMM_{rat}$ was ~140 $s^{-1}$. These results indicate that MgADP binds four times more strongly to β $MHC_{pig}$ than to β $MHC_{rat}$. For comparison, the maximum rate constant for dissociation of acto-α $HMM_{rat}$ was ~600 $s^{-1}$.

Although thin filament protein expression differs between skeletal muscle and myocardium, these proteins did not differ between species in either skeletal or cardiac muscle cells, and thus, the faster shortening speeds of rat muscle cells was mainly due to substitutions in the β-cardiac MHC's of both species. While loop 1 is the same size in human and rat β-MHC's, the sequences differ in a T/S substitution in residue 210. Since it seems unlikely that the substitution of one hydroxylated residue for another could account for a 3-fold difference in the kinetics of turnover of these molecular motors, the inventors performed additional mechanical experiments using β-cardiac MHC-containing cardiac myocytes from pig, dog and rat, which have identical loop 1 residues (DRSKKDQTPGK). Using flash photolysis of caged $Ca^{2+}$ (DM-nitrophen for activation; diazo-2 for relaxation) the inventors found that the rates of activation and relaxation differed significantly in these cells, with pig myocytes being slowest ($k_{activ}$=1.6 $s^{-1}$; $k_{relax}$=2.0 $s^{-1}$), dog myocytes next fastest ($k_{relax}$=2.4 $s^{-1}$), and rat myocytes fastest of all ($k_{activ}$=3.8 $s^{-1}$; $k_{relax}$=5.0 $s^{-1}$). These results indicate that in myocytes containing β MHC exhibiting 100% identity in loop 1, there are profound differences in the kinetics of chemomechanical transduction. Thus, while loop 1 appears to be an important determinant of kinetic properties of myosin (18,69), it is clear from the present results that other factors account for the differences in kinetics between MHC's, particularly between β-cardiac MHC's in various species.

A major thrust of the present invention is that loop 1 affects ADP dissociation from myosin, an effect which might be mediated by electrostatic interactions of loop 1 with another region(s) of the MHC. To explore a possible structural basis for such interactions, the inventors compared sequences of various MHC genes to identify regions that exhibit sufficient divergence to account for functional differences between myosin isoforms and enough charge density to provide complementary binding for loop 1. Once a candidate region was identified, the inventors examined several characteristics including location and surface distribution of corresponding residues using the crystallographic structure of chicken pectoralis MHC (51). The combined analysis suggested just one region that fit the profile the inventors sought, residues 323-351, which was termed the "interactive microdomain" (IMD)—the table below shows sequences of this region for various MHC isoforms.

|  | 316 | 317 | 318 | 319 | 320 | 321 | 322 | 323 | 324 | 325 | 326 | 327 | 328 | 329 |
|---|---|---|---|---|---|---|---|---|---|---|---|---|---|---|
| Chicken Pect (SEQ ID NO:19) | S | E | G | E | I | T | V | P | S | I | D | D | Q | E |
| Rat β Card (SEQ ID NO:20) | — | Q | — | — | T | — | — | A | — | — | — | — | S | — |
| Hum β Card (SEQ ID NO:21) | — | Q | — | — | T | — | — | A | — | — | — | — | A | — |
| Pig β Card (SEQ ID NO:22) | — | Q | — | — | T | — | — | A | — | — | — | — | A | — |
| Rat α Card (SEQ ID NO:23) | — | Q | — | — | V | S | — | A | — | — | — | — | S | — |
| Mouse α Card (SEQ ID NO:24) | — | Q | — | — | V | S | — | A | — | — | — | — | S | — |
| Rabbit 2x (SEQ ID NO:25) | — | — | — | — | — | — | — | — | — | — | — | — | S | — |
|  | 330 | 331 | 332 | 333 | 334 | 335 | 336 | 337 | 338 | 339 | 340 | 341 | 342 | 343 |
| Chicken Pect (SEQ ID NO:19) | E | L | M | A | T | D | S | A | I | D | I | L | G | F |
| Rat β Card (SEQ ID NO:20) | — | H | — | — | — | — | — | — | F | — | V | — | — | — |
| Hum β Card (SEQ ID NO:21) | — | — | — | — | — | N | — | F | — | V | — | — | — | — |

-continued

| | | | | | | | | | | | | | |
|---|---|---|---|---|---|---|---|---|---|---|---|---|---|
| Pig β Card (SEQ ID NO:22) | — | — | — | — | — | — | N | — | F | — | V | — | — | — |
| Rat α Card (SEQ ID NO:23) | — | — | L | — | — | — | — | — | F | — | V | — | — | — |
| Mouse α Card (SEQ ID NO:24) | — | — | L | — | — | — | — | — | F | — | V | — | S | — |
| Rabbit 2x (SEQ ID NO:25) | — | — | — | — | — | — | — | — | — | — | — | — | — | — |

| | 344 | 345 | 346 | 347 | 348 | 349 | 350 | 351 | 352 | 353 | 354 | 355 | 356 | 357 |
|---|---|---|---|---|---|---|---|---|---|---|---|---|---|---|
| Chicken Pect (SEQ ID NO:19) | S | A | D | E | GAP | T | A | I | Y | GAP | L | T | G | A |
| Rat β Card (SEQ ID NO:20) | T | P | E | — | K | N | S | I | — | K | — | — | — | — |
| Hum β Card (SEQ ID NO:21) | T | S | E | — | — | N | S | M | — | — | — | — | — | — |
| Pig β Card (SEQ ID NO:22) | T | S | E | — | — | N | S | M | — | — | — | — | — | — |
| Rat α Card (SEQ ID NO:23) | T | — | E | — | — | A | G | V | — | — | — | — | — | — |
| Mouse α Card (SEQ ID NO:24) | T | — | E | — | — | A | G | V | — | — | — | — | — | — |
| Rabbit 2x (SEQ ID NO:25) | T | S | — | — | R | V | S | — | — | — | — | — | — | — |

Sequences corresponding to the IMD region of different MHC isoforms are shown above, aligned using the numbering system for chicken pectoralis myosin (51). Pig β-cardiac and rabbit 2x MHC's were obtained in the inventors' laboratory and were predicted from cDNA's generated by RT-PCR/cloning of electrophoretically characterized muscle fibres (53) and subsequent sequencing. The rest of the sequences were available gene bank sequences.

Generation of Mice with Mutant MHC's. In part, the present invention is directed to transgenic mice expressing MHC's in which loop 1, the IMD, or both have been mutated. The inventors' general approach to this process involves the use of knock-in methodologies, which are well known in the art.

Using mouse α MHC as background, the inventors can insert the β MHC ATPase loop, which is identical in rat and pig (human), yielding an α MHC$^{\beta loop}$ mouse. If the ATPase loop is a primary determinant of nucleotide turnover kinetics, insertion of loop 1 from the much slower rat and pig β MHC's should slow the ATPase activity and in vitro motility of the α MHC, as well as slowing the contraction kinetics of myocytes expressing α MHC$^{\beta loop}$.

Using the α MHC$^{\beta loop}$ mouse as background, the inventors can develop at least two additional mice by inserting the interactive microdomain (IMD) from rat β MHC (an α MHC$^{\beta loop/rat\ \beta IMD}$ mouse) and from pig β MHC (an α MHC$^{\beta loop/pig\ \beta IMD}$ mouse). These lines are particularly valuable to demonstrate how the IMD modulates nucleotide turnover kinetics. Because rat β MHC exhibits faster kinetics than pig β MHC, the inventors predict that turnover kinetics will be faster for α MHC$^{\beta loop/rat\ \beta IMD}$ than for α MHC$^{\beta loop/pig\ \beta IMD}$. Mutations can be introduced by selective knock-ins in mouse myocardium on a murine α MHC background. Using this model, (i) myosin function can be assessed from mechanical measurements on contracting cardiac myocytes and from biochemical and in vitro motility measurements on isolated proteins, and (ii) the mutations will be done in cardiac myosin, which is the most physiologically relevant MHC for studies of this type. These mutants are valuable to demonstrate that variations in loop 1 and IMD sequence account for much, if not all, of the differences in kinetic characteristics of α and β MHC's.

In addition to loop and IMD replacements, it is possible to systematically reverse the electrostatic charge of first loop 1 and then the IMD by mutagenesis using the α MHC$^{\beta loop/pig\ \beta IMD}$ construct. These mutants are particularly useful to determine how electrostatic interactions between the loop and IMD are required for nucleotide dissociation from the binding pocket. The inventors predict that kinetics will be faster when attractive interactions are increased and slower when such interactions are reduced. Lysines 207,208 in loop 1 of the α MHC$^{\beta loop/pig\ \beta IMD}$ can be changed to glutamic acids to disrupt the interaction of loop 1 with the IMD—in this case the inventors predict that kinetics will be slowed due to reduced attraction of the loop and IMD. In contrast, replacement of lys348 in the IMD with glutamic acid should enhance its electrostatic attraction to loop 1 and thereby speed kinetics.

The kinetics of the actin-activated ATPase vary nearly 10-fold among the myosin isoforms expressed in mammalian cardiac muscle. From a systems design perspective, this variation provides a means for tuning the characteristics of myosin to assure close correspondence to requirements for muscle work rate (or power) and the rates of onset and relaxation of force. In this regard, it is likely that the diminished capacity of the heart to perform work in diseases such as end-stage congestive heart failure involves depression of myosin turnover kinetics, resulting in a mismatch between kinetics and the requirements for myocardial work.

The inventors have identified that residues within loop 1 interact electrostatically with residues in an "interactive micro-domain" (residues 323-351), or IMD, which is adjacent to the loop and also the nucleotide binding pocket, and this interaction influences the rates of nucleotide dissociation from the pocket. As the strength of interaction increases due to isoform-specific changes in charge or primary sequence of either the loop or the IMD, the inventors propose that loop 1 is drawn toward the nucleotide binding pocket, resulting in faster rates of nucleotide turnover in the binding site. Thus, by affecting the rate of ADP dissociation, loop 1 and the IMD would be expected to be important determinants of muscle power and cross-bridge turnover kinetics. This concept my be further confirmed by assaying the mutant MHCs described herein, for example, by biochemical, in vitro motility and mechanical measurements to assess turnover kinetics of (i) myosin isoforms having natural variations in charge or sequence in loop 1 or the IMD, (ii) myosins in which loop 1 and/or the IMD have been replaced with the corresponding sequence(s) from other cardiac myosin isoforms exhibiting different turnover kinetics, or (iii) myosins in which electrostatic charges in loop 1 or the IMD have been reversed.

Further mutant lines can be created as follows:

Rat/pig β loop1 mutation of the mouse α MHC gene. The α MHC gene was cloned from a mouse strain SV129 BAC library (Genome Systems) and a 4.4 kb Eco RI fragment containing exon 7 though exon 12 was identified. Site-directed mutagenesis was used to substitute the rat/pig β loop 1 for the α loop using a 1.4 kb Eco RI-Eco RV fragment containing exon 7 as a template. A targeting vector containing the rat/pig β loop 1 substitution may be constructed according to techniques known in the art and introduced into mouse embryonic stem cells to produce a transgenic animal.

Pig and rat β IMD mutations of the mouse α MHC$^{\beta loop}$ line. Whole plasmid synthesis (WHOPS) site-directed mutagenesis (73) may be used to substitute rat or pig β IMD's for the mouse α IMD. Comparison of the IMD regions for each isoform is shown below; amino acids changes are shown in bold.

esis. To exclude any PCR-generated artifacts, the entire 1 kb Bgl II fragment can be sequenced prior to reintroducing it into the β loop 1 targeting vector.

Development of mutant loop 1 and IMD mouse lines. Each of the mouse lines may be developed using the transgenic strategy described above. Linearized targeting vector may be electroporated into mouse embryonic stem (ES) cells (R1 or AB2.2). Transformed ES cells may be selected for neomycin resistance (Neo$^r$) with G418. Neo$^r$ cells, may be selected, replicated and expanded. DNA isolated from the Neo$^r$ ES clones may be digested with restriction enzymes that will allow detection of insertion by homologous recombination, transferred to a charged nylon membrane by Southern blotting, and hybridized to radio-labeled DNA probes that lie outside the region included in the targeting vector. Neo$^r$ ES clones that have arisen by homologous recombination will exhibit a new hybridizing fragment of a diagnostic size. Neo$^r$ ES clones that have arisen from random integration of the targeting vector will exhibit only the endogenous hybridizing fragment. Each of the knock-in analyses may use the same restriction enzyme digest and probes. Correctly targeted ES clones will contain the planned mutation and the selectable markers PGK-neo and TK flanked by loxP sites. Correctly targeted ES clones will be expanded and micro-injected into mouse C57B1/6 blastocysts according to transgenic procedures known in the art.

As noted before, chimeric mice may then be mated to C57B1/6 partners and the resulting agouti pups analyzed by Southern blot for the presence of the knock-in chromosome. The PGK-neo/TK cassette may subsequently be "floxed" or removed with Cre recombinase mediated recombination by crossing heterozygous knock-in mice with mice that express Cre recombinase in the male germline under the control of the protamine promoter (46). Cre-mediated recombination will occur in spermatocytes, and recombined alleles will be incorporated into the fertilized egg. The resulting animals will transmit the recombined alleles to their progeny. PCR and Southern blot analysis may then be used to identify mice carrying the "floxed" knock-in chromosome.

The resulting animals and tissues therefrom may be analyzed by the techniques described above, some of those techniques presented in more detail below.

| | EXON 11 | | EXON 12 |
|---|---|---|---|
| Mouse α | A S I D D S E E L L A T D (SEQ ID NO:26) | Mouse α | S A F D V L S F T A E E K A G V (SEQ ID NO:29) |
| Pig β | A S I D D S E E L M A T D (SEQ ID NO:27) | Pig β | N A F D V L G F T A E E K N G V (SEQ ID NO:30) |
| Rat β | A S I D D S E E H M A T D (SEQ ID NO:28) | Rat β | S A F D V L G F T P E E K A S I (SEQ ID NO:31) |

Since the IMD is encoded by exons 11 and 12, two rounds of mutagenesis per isoform will be necessary to make the planned changes. Primers can be generated to introduce the planned amino acid substitutions, as well as translationally silent restriction sites that are included to aid in the identification of the mutated fragments. A 1 kb Bgl II fragment that contains exons 11 and 12 can be excised from the β loop 1 targeting vector and sub-cloned into the vector pSP73 (Promega). This plasmid can be used as the template in the whole plasmid synthesis (WHOPS) site-directed mutagen- Single cardiac myocytes. Mechanical measurements may be performed on skinned myocytes from mouse, rat or pig hearts. Ventricular myocytes are prepared as described earlier (60) and stored at 4° C. until used in an experiment. Skinned myocytes are necessary to allow control of solutions bathing the myofibrils, which is critical for precise buffering of free [Ca$^{2+}$] and for infusion of caged compounds (40,60).

Apparatus for mechanical measurements on skinned muscle cells. The experimental chamber for mechanical studies on cardiac myocytes is one routinely used in the art (60). Force is measured with a transducer having sensitivity of 20 mV/mg, resolution of <50 µg, and resonant frequency of ~600 Hz (Model 403, Aurora). A torque motor (Model 6350, Aurora) is used to introduce length changes (within 1.5 ms) for dynamic measurements. Force and length signals are digitized at 10 kHz using a 12-bit A/D converter and then displayed and stored on computer using custom software based on LabView for Windows. Images of the myocytes are continuously recorded on video tape using microscopy, a Panasonic video camera (WV-B1600) and a JVC VHS recorder (HR-s6600u) (21,66). After the experiment, the tape is played back to measure mean sarcomere length while the myocyte is relaxed and during activation.

Attachment of skinned myocytes to apparatus. For isometric measurements, skinned ventricular myocytes are glued with silicone adhesive (Aquarium Sealant, Dow Corning) to stainless steel shafts from the active elements of the force transducer and motor. Once the silicone cures, the myocyte is transferred to relaxing solution and sarcomere length is adjusted to 2.3 µm using on-line video microscopy. For dynamic measurements (force-velocity relationships, $k_{Ca}$, $k_{ADP}$, $k_r$) in which end compliance must be very low, muscle cells are attached using a modification of the method used by the inventors for skeletal muscle fibers (35). While in relaxing solution, each end of the myocyte is placed in a stainless steel trough (27 ga), where the ends are secured by overlaying a 0.5 mm length of 5-0 monofilament suture, which is secured with two loops of 10-0 monofilament. Preparations with slack length of 150-200 µm are used, since this provides sufficient length to grasp the ends with forceps for transfer to the troughs. A 30 µm length of each end of the preparation is covered by the 5-0 suture, leaving more than 100 µm exposed to the solution. Because mouse ventricular myocytes don't usually exceed 100 µm, the preparations used in these experiments are in most cases two myocytes in series. Given the very low compliance of these preparations and uniform striation patterns during maximal activation, the inventors conclude that the structural integrity of the intercalated disc is maintained during maximal activations.

Maximum isometric force. Isometric tension may be measured at mean sarcomere length of 2.3 µm and at 15° C. during maximal activation in solution of pCa 4.5 (60). The uniformity of SL in these preparations presumably results from low-compliance attachments to the apparatus. Routine monitoring of SL and uniformity in these preparations very quickly reveals any compliance in the attachments to the apparatus, and in such cases, the preparation is discarded. Mean SL in the inventors' skinned myocyte preparations typically decreases less than 5% in the transition from rest to maximum isometric tension (60).

Rates of tension development ($k_{ADP}$, $k_{Ca}$) and tension relaxation ($k_r$). Rates of tension development and relaxation can be measured at 15° C. in skinned muscle preparations by recording the time course of tension rise following flash photolysis of compounds (33,47,48,72). Photolysis is performed in an 18 µl quartz-walled chamber, which is irradiated with light from a flash lamp consisting of a xenon short arc tube (Chadwick-Helmuth) a UG11 band pass filter (300-350 nm), a 305 nm cut-off filter (Oriel 305) and condensing lenses that produce a 0.6 cm×0.4 cm oval beam. A power supply generates a single adjustable pulse that produces a 1 ms UV flash of up to 100 mJ, with less than 10% variation between flashes.

Tension development may be measured in at least two ways. Typically, caged $Ca^{2+}$ (DM-nitrophen; Molecular Probes) are used to rapidly increase $[Ca^{2+}]$ in the vicinity of the myofibrils from relaxing to near maximal levels (47). DM-nitrophen rapidly (<2 ms) releases $Ca^{2+}$ when exposed to a flash of UV light ($\lambda \approx 360$ nm) due to a decrease in $Ca^{2+}$ binding affinity from 5 nM to 3 mM (refs in 47). The tension transient recorded upon photolysis is fit with a single exponential of the form, $F_t = F_o (1-e^{-kt})$, where $F_t$ is force at time t, $F_o$ is maximum force, and k is $k_{Ca}$, the rate constant of force development in response to photogeneration of $Ca^{2+}$. A second independent method involves photorelease of MgADP from caged ADP (33).

If $k_{Ca}$ varies with MHC content, it is possible to assess whether this is due to effects on the force-generating step by measuring the kinetics of the $P_i$ release step using caged $P_i$ (72). The inventors synthesize their our own caged $P_i$ and have found that a single maximal flash results in 21% conversion of caged $P_i$ to free $P_i$, i.e., 5 mM caged $P_i$ in solution results in photogeneration of ~1.0 mM $P_i$. Final $[P_i]$ in the photolysis chamber is calculated as the sum of $P_i$ produced by photolysis plus $P_i$ present in the solution due to addition prior to photolysis. Thus, assessment of $k_{Pi}$ at 20 mM $P_i$ is done by photogenerating 1.0 mM $P_i$ in an activating solution that already contains 19.0 mM free $P_i$. Calculations of total $P_i$ in skinned muscle preparations will take into account contaminant $P_i$ and $P_i$ contributed by the muscle preparation during steady activation (11). Commercial software is used to perform non-linear least-squares fits of data with exponential equations, and simulations are performed by numerical solutions of differential equations using the Runge-Kutta algorithm (72).

The rate constant of tension relaxation ($k_r$) may be determined by recording relaxation in response to photolysis of the caged $Ca^{2+}$ chelator diazo-2. Photolysis rapidly (<0.2 ms) converts diazo from a chelator of low affinity (2.2 mM) to one of much higher affinity (73 nM) (57). Myocytes are first loaded with 2 mM diazo-2 and then transferred to silicone oil for photolysis.

$V_{max}$, force-velocity relationship and power-load relationship. The slack test method may be used to measure unloaded shortening velocity ($V_{max}$) in skinned muscle cells at 15° C. Measurements of force-velocity and power-load relationships employ an electronic servo system to control load (66), i.e., myocyte force is kept constant by comparing force to a computer-generated command voltage. After 100-250 ms of isotonic shortening, the myocyte is slackened to obtain the force baseline and then re-extended to its initial length. As many as 20 force clamps can be imposed on a myocyte before tension generating capability declines significantly, i.e., in most myocytes, maximum tension declines by <10%.

Relative force during isotonic shortening is calculated by dividing absolute load (P) by maximum isometric force ($P_o$) obtained under the same conditions (35). Since shortening traces are linear during maximal activation, velocity is determined by a least-squares linear regression fit to the length trace. Hyperbolic force-velocity curves may be fit to force-velocity data using the Hill (22) equation:

$$(P+a)(V+b) = (P_o+a)b, \qquad (1)$$

where P is force during shortening at velocity V, $P_o$ is peak isometric force, and a and b are constants with dimensions of force and velocity. Power-load curves may be obtained by multiplying force×velocity at each point on the force-velocity curve. Optimum force for power output ($F_{opt}$) is calculated as (74):

$$F_{opt} = (a^2 + a \cdot P_o)^{1/2} - a. \qquad (2)$$

One-way, repeated-measures ANOVA are used to determine whether there are significant differences in force-velocity or power-load relationships due to MHC content. A Student-Newman-Keuls test may be used as a post hoc test to assess differences among means.

Quantitative SDS-PAGE. Methods for quantifying high and low molecular weight protein subunits in skinned myocyte were previously developed and are routine in the art (21,60).

Actin-activated ATPase activity and nucleotide turnover. ATPase activities may be assayed using standard protocols (62). Stopped-flow methods may be used to assess rates of myosin nucleotide dissociation (56,65). Rates of MgATP-induced dissociation of acto-HMM and acto-HMM-ADP may be measured 15° C. in a micro-volume Stopped-Flow Reaction Analyzer SX.18MV (1.6 ms dead time) with Pro/Kineticist (Applied Photophysics, England). Rates of dissociation of acto-HMM in the presence and absence of MgADP may be monitored by changes in light scattering at 340 nm (56). Acto-HMM dissociation by MgATP is initiated by rapidly mixing a solution of 4 µM actin, 2 µM HMM and 1 µM AP$_5$A and salts (100 mM KCl, 25 mM MOPS, 1 mM EGTA, 1 mM MgCl$_2$, 1 mM DTT) with solutions containing 0.02, 0.05, 0.1, 0.2, 0.5, 1.0, 2.0, 5.0 and 10.0 mM MgATP (identical salts). To measure rates of MgADP dissociation from acto-HMM-MgATP, 40 or 180 µM MgADP may be added to the acto-HMM-AP$_5$A solution before mixing with the MgATP solutions. Exponential fits to the time course of light scattering may be performed using software routines from the stopped-flow device manufacturer. Typically, 3-6 stopped-flow records are averaged to obtain a rate for a given MgATP concentration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Bauer, C. B., Holden, H. M., Thoden, J. B., Smith, R., and raiment, I., (2000). X-ray structures of the Apo and MgATP-bound states of *Dictyostelium discoideum* myosin motor domain. J. Biol. Chem. 275, 38494-38499.

Bernstein, S. I., and Milligan, R. A. (1997). Fine tuning a molecular motor: The location of alternative domains in the *Drosophila* myosin head. J. Mol. Biol. 271, 1-6.

Dominguez, R., Freyzon, Y., Trybus, K. M., and Cohen, C. (1998). Crystal structure of a vertebrate smooth muscle myosin motor domain and its complex with the essential light chain: visualization of the pre-power stroke state. Cell 94, 559-571.

Fisher, A. J., Smith, C. A., Thoden, J. B., Smith, R., Sutoh, K., Holden, H. M. and Rayment, I. (1995). X-ray structures of the myosin motor domain of *Dictyostelium discoideum* complexed with MgADP.BeF$_x$ and MgAD-P.AlF$_4^-$. Biochemistry 34, 8960-8972.

Geeves, M. A., and Holmes, K. C. (1999). Structural mechanism of muscle contraction. Ann. Rev. Biochem. 68, 687-728.

Gulick, A. M. and Rayment, I. (1997). Structural studies on myosin II: communication between distant protein domains. Bioassays 19, 561-569.

Houdusse, A. and Cohen, C. (1996). Structure of the regulatory domain of scallop myosin at 2 A resolution: implications for regulation. Structure 4, 21-32.

Houdusse, A., Kalabokis, V. N., Himmel, D., Szent-Gyorgyi, A. G. and Cohen, C. (1999). Atomic structure of Scallop Myosin Subfragment S1 Complexed with MgADP: A Novel Conformation of the Myosin Head. Cell 97, 459-470.

Kambara, t., Rhodes, T. E., Ikebe, R., Yamashita, M, White, H. D., and Ikebe, M. (1999). Functional significance of the conserved residues in the flexible hinge region of the myosin motor domain. J. Biol. Chem. 274, 16400-16406.

Johnson, K. A. and Taylor, E. W. (1978). The intermediate states of subfragment 1 and acto-subfragment 1 ATPase—a reevaluation of the mechanism. Biochemistry 17, 3432-3442.

Rayment, I., Rypniewski, W. R., Schmidt-Base, K., Smith, R., Tomchick, D. R., Benning, M. M., Winkelmann, D. A., Wesenberg, G., and Holden, H. M. (1993). Three-dimentional structure of myosin sub-fragment-1: a molecular motor. Science 261, 50-58.

Rovner, A. S., Freyzon, Y., and trybus, K. M. (1997). An insert in the motor domain determines the functional properties of expressed smooth muscle myosin isoforms J. Muscle Res. Cell Motil. 18, 103-110.

Sant'Ana Pereira, J. A. A., Pavlov, D., Nili, M., Greaser, M., Homsher, E. and Moss, R. L. (2001). Kinetic differences in myosins with identical loop 1 sequences. J. Biol. Chem. 276, 4409-4415.

Sant'Ana Pereira, J. A. A., Archer, M., Pavlov, D., Nili, M., Homsher, E. and Moss, R. L. (2002). Kinetics of acto-myosin (HMM) interaction in rat cardiac a and rat β motor proteins: structural-functional implications. (this issue)).

Siemankowski, R., and White, H. D. (1984). J. Biol. Chem. 259, 5045-5053.

Smith, C. A. and Rayment, I. (1996). X-ray structure of the magnesium(II)·ADP·vanadate complex of the *Dictyostelium discoideum* myosin motor domain to 1.9 A resolution. Biochemistry 13, 3837-3840.

Spudich (1994). How molecular motors work. Nature 372, 515-518.

Strang, K., Sweitzer, N. K., greaser, M. L., and Moss, R. L. (1994). Circ. Res. 74, 542-549.

Sweeney, H. L., Rosenfeld, S. S., Brown, F., Faust, L., Smith, J., Xing, J., Stein, L. A., and Sellers, J. (1998). Kinetic tuning of myosin via a flexible loop adjacent to the nucleotide binding pocket. J. Biol. Chem. 273, 6262-6270.

Kraulis, P. (1991). MOLSCRIPT—A program to produce both detailed and schematic plots of protein structure. J Appl Crystallogr 24, 946-950.

Marti-Renom, M. A., Stuart, A., Fiser, A., Sánchez, R., Melo, F., Sali, A. (2000). Comparative protein structure modeling of genes and genomes. Annu. Rev. Biophys. Biomol. Struct. 29, 291-325.

Merrit, E., and Murphy, M. E. P. (1994) Raster3D version2.0: a program for photorealistic molecular graphics. Acta Crysttalogr. Sect.D Biol. Crystallogr. 50, 869-873

Merritt, E. A., Bacon, D. J. (1997). Raster3D photorealistic molecular graphics. Methods Enzymol. 277, 505-524.

Roussel, A., and Cambilau, C. (1989). Turbo-Frodo in Silicon graphicsGeometry Partners Directory (Mountain View, Canada: Silicon Graphics), pp. 77-78.

Schiaffino, S. & Reggianni, C. (1996). Physiol. Rev. 76, 371-423.

Rayment, I., Rypniewski, W. R., Schmidt-Base, K., Smith, R., Tomchick, D. R., Benning, M. M., Winkelmann, D. A., Wesenberg, G. and Holden, H. M. (1993). Science 261, 50-58

Goodson, H. V., Warrick, H. M. & Spudich, J. A. (1999). J. Mol. Biol. 287, 173-185.

Spudich, J. (1994). Nature 372, 515-518.

Uyeda, T. Q., Ruppel, K. M. and Spudich, J. A. (1994). Nature 368, 567-569

Rovner, A. S., Freyzon, Y., & Trybus, K. M. (1995). J. Biol. Chem. 270, 30260-30263.

Umemoto, S. & Sellers, J. (1990). J. Biol. Chem. 265, 14864-14869.

Siemakowski, L. M., Wiseman, M. O. & White, H. D. (1985). Proc. Natl. Acad. Sci. USA 82, 685-662.

Kelley, C., Takahashi, M., Yu, J. H. & Aldstein, R. (1993). J. Biol. Chem. 268, 12848-12854.

Rovner, A. S., Freyzon, Y. & Trybus, K. M. (1997). J. Mus. Res. Cell Motil. 18, 103-110.

Sweeney, H. L., Rosenfeld, S. S, Brown, F., Faust, L., Smith, J., Xing, J., Stein, L. A. & Sellers, J. (1998). J. Biol. Chem. 273, 6262-6270.

Hill, A. V. (1950). Science Progress XXXVIII 150, 209-230.

Rome, L. C., Funke, R., Alexander, R. McN., Scott, H., Freadman, M. A. (1988). Nature 355, 824-827.

Haddad, F., Masatsugu, M., Bodell, P. W., Qin, A., McCue, S. A. & Baldwin, K. M. (1997). J. Mol. Cardiol. 29, 559-569.

Strang, K. T., Sweitzer, N. K., Greaser, M. L. & Moss, R. L. (1994). Circ. Res. 74, 542-549.

Sant'Ana Pereira, J. A. A., Greaser, M. L. & Moss, R. L. (1999). Submitted

Sant'Ana Pereira, J. A. A., Wessels, A., Nijtmans, L., Moorman, A. & Sargeant, A. J. (1995). J. Mus. Res. Cell Motil. 16, 21-34.

Chromazynski, P. & Sacchi, N. (1987). Anal. Biochem. 162, 156-159.

Sant'Ana Pereira, J. A. A., Ennion. S., Sargeant, A. J., Moorman, A. F. & Goldspink, G. (1997). Pflugers Arch. 435, 151-163.

Houk, T. W. Jr & He, K. (1974). Anal. Biochem. 62, 66-74.

Margossian & Lowey (1978)

Carter, S. G. & Karl, D. W. (1982). J. Biochem. Biophys. Meth. 7, 7-13.

Johnson, K. A. & Taylor, E. W. (1978). Biochem. 17, 3432-3442.

Siemankowski, R. & White, H. D. (1984). J. Biol. Chem. 259, 5045-5053.

Huxley, A. (1957). Prog. Biophys Chem. 7, 255-317.

Moss, R. L., Diffee, G. M. & Greaser, M. L. (1995). Reviews of Physiol. Biochem. Pharmacol. 126, 1-63.

Sata, M., Sugiura, S., Yamashita, H., Momomura, S. & Serizawa, T. (1993). Circ. Res. 73, 696-704.

Lowey, S., Waller, G. & Trybus, K. (1993). Nature 365, 454-456.

Moss, R. L. (1992). Circ. Res. 70, 865-884.

Bottinelli, R., Betto, R., Schiaffino, S. & Reggiani, C. (1994). J. Physiol. (Lond). 478, 241-349.

Sweeney, L. (1995). Biophys. J. 68, 112S-119S.

Gulick, J., Hewett, T. E., Klevitsky, R., Buck, S. H., Moss, R. L. & Robbins, J. (1997). Circ. Res. 80, 655-664.

Dong, W. J., Rosenfeld, S. S., Wang, C. K. Gordon, A. M. & Cheung, H. C. (1996). J. Biol. Chem. 271, 688-694.

Van Buren, P., Harris, D. E., Alpert, N. R. & Warshaw, D. M. (1995). Cirsc. Res. 77 (2), 439-444

Mocz, G., Szilagyi, L., Lu, C., Fabian, M. & Gergely, J. (1984). Eur. J. Biochem. 145, 221-229.

Bobkov, A. A., Bobkova, E. A., Lin, S-H & Reisler, E. (1996). Proc. Natl. Sci. USA. 93, 2285-2289.

ADDITIONAL REFERENCES

1. Alpert, N R and L A Mulieri (1981). Heat, mechanics and myosin ATPase in normal and hypertrophied heart muscle. Fed Proc 41:192-198.
2. Anderson, P A W, N N Malouf, A E Oakeley, E D Pagani and P D Allen (1991). Troponin T isoform expression in humans. A comparison among normal and failing adult heart, fetal heart, and adult and fetal skeletal muscle. Circ Res 69:1226-1233.
3. Barany, M (1967). ATPase activity of myosin correlated with speed of muscle shortening. J Gen Physiol 50: 197-216.
4. Berman, M R, C C Lord and D W Maughan (1988). Force transient time course in heart muscle with high and low V1 V3 myosin isoenzyme ratio. J Mol Cell Cardiol 20:679-687.
5. Bonne, G, L Carrier, P Richard, B Hainque and K Schwartz (1998). Familial hypertrophic cardiomyopathy: from mutations to functional defects. Circ Res 83:580-593.
6. Bottinelli, R, R Betto, S Schiaffino and C Reggiani (1994). Unloaded shortening velocity and myosin heavy chain and alkali light chain isoform composition in rat skeletal muscle fibres. J Physiol 481:663-675.
7. Buck, S H, P J Konyn, J Palermo, J Robbins and R L Moss (1999). Altered kinetics of contraction of mouse atrial myocytes expressing ventricular myosin regulatory light chain. Am J Physiol 276:H1167-H1171.
8. Brenner, B. (1986). The cross-bridge cycle in muscle. Basic Res Cardiol 81:1 15.
9. Chen, J, S W Kubalak, M Susumu, K D Becker, R Hickey, J Ross Jr and K R Chien (1998). Unique requirement of myosin light chain-2v in heart function and morphogenesis. J Biol Chem 273:1252-1256.
10. Chizzonite, R A, A W Everett, W A Clark, S Jakovcic, M Rabinowitz, and R Zak (1982). Isolation and characterization of two molecular variants of myosin heavy chain from rabbit ventricle. J Biol Chem 257:2056-65.
11. Cooke, R and E Pate (1985). The effects of ADP and phosphate on the contraction of muscle fibers. Biophys J 48:789-98.
12. Coviello, D A, R Bottinelli, A Trojani, E Panucci, M R Iascone, R Bertorelli, P Spinto, C Autore, A Biagini, C, Reggiani and F Ajmar (1997). Molecular and functional analysis of mutant sarcomeric gene responsible for familial hypertrophic cardiomyopathy. Am J Human Genet 61:A329
13. deTombe, P P (1998). Altered contractile function in heart failure. Cardiovasc Res 37:367-380.
14. Diffee, G M, J R Patel, F C Reinach, M L Greaser and R L Moss (1996). Altered kinetics of contraction in skeletal muscle fibers containing a mutant myosin regulatory light chain with reduced divalent cation binding. Biophys J 71:341-350.
15. Fentzke, R C, S H Buck, J R Patel, H Lin, R J Solaro, R L Moss, and J M Leiden (1999). Impaired cardiomyocyte relaxation and diastolic function in transgenic mice expressing slow skeletal troponin I in the heart. J Physiol 517:143-157.
16. Fitzsimons, D P, J R Patel and R L Moss (1998). Role of myosin heavy chain composition on kinetics of force development and relaxation in rat myocardium. J Physiol 513:171-183.

17. Geisterfer-Lowrance, A A T, M Christe, D A Conner, J S Ingwall, F J Schoen, C E Seidman and J G Seidman (1996).A mouse model of familial hypertrophic cardiomyopathy. Science 272:731-734.
18. Geeves, M A and K C Holmes (1999). Structural mechanism of muscle contraction. Ann Rev Biochem 68:687-728.
19. Gordon, A M, E Homsher and M Regnier (2000). Regulation of contraction in striated muscle. Physiol Rev 80:853-924.
20. Gregg, R G, A Messing, C Strube, M Beurg, R L Moss, M Behan, M Sukhareva, S Haynes, J Powell, R Coronado, and P A Powers (1996). Absence of the β subunit (cchb1) of the skeletal muscle dihydropyridine receptor alters expression of α1 subunit and eliminates excitation-contraction coupling. Proc Natl Acad Sci USA 93:13961-966.
21. Gulick, J, T E Hewett, R Klevitsky, S H Buck, R L Moss, and J Robbins (1997). Transgenic remodeling of the regulatory myosin light chains in mammalian heart. Circ Res 80:655-664.
22. Hill, A V (1938). The heat of shortening and the dynamic constants of muscle. Proc R Soc London B 126:136-95.
23. Hofmann, P A, J M Metzger, M L Greaser, R L Moss (1990). The effects of partial extraction of light chain 2 on the Ca2+ sensitivities of isometric tension, stiffness and velocity of shortening in skinned skeletal muscle fibers. J Gen Physiol 95:477-498.
24. Hoh, J F Y, G H Rossmanith, L J Kwan and A M Hamilton (1988). Adrenaline increases the rate of cycling of cross bridges in rat cardiac muscle. Circ Res 62:452-461.
25. Homsher, E, B Kim, A Bobkova and L S Tobacman (1996). Calcium regulation of thin filament movement in an In Vitro motility assay. Biophysical Journal 70:1881-1892.
26. Homsher, E, D M Lee, C Morris, D Pavlov and L S Tobacman (2000). Regulation of force and unloaded sliding speed in single thin filaments: effects of regulatory proteins and calcium. J Physiol 524:233-243.
27. Huang, X P, Y O Pi, K J Lee, A S Henkel, R G Gregg, P A Powers and J W Walker (1999). Cardiac troponin I gene knock-out: A mouse model of myocardial troponin I deficiency. Circ Res 84:1-8.
28. Jones, W K, I L Grupp, T Doetschman, G Grupp, H Osinska, T E Hewett, G Boivin, J Gulick, W A Ng and J Robbins (1996). Ablation of the murine α myosin heavy chain gene leads to dosage effects and functional deficits in the heart. J Clin Invest 98:1906-1917.
29. Kelley, C, M Takahashi, J H Yu and R Adelstein (1993). An insert of seven amino acids confers functional differences between smooth muscle myosins from the intestines and vasculature. J Biol Chem 268:12848-12854.
30. Krueger, J W and A Denton (1992). High resolution measurement of striation patterns and sarcomere motions in cardiac muscle cells. Biophys J 61:129-144.
31. Hoh, J F Y, P A McGrath and P T Hale (1978). Electrophoretic analysis of multiple forms of cardiac myosin: effect of hypophysectomy and thyroxine replacement. J Mol Cell Cardiol 10:1053-1076.
32. Lowey, S, G S Waller and K M Trybus (1993). Skeletal muscle myosin light chains are essential for physiological speeds of shortening. Nature 365:454-456.
33. Lu, Z, R L Moss, J W Walker (1993). Tension transients intiated by photogeneration of MgADP in skinned skeletal muscle fibers. J Gen Physiol 101:867-888.
34. Lyons, G E, S Schiaffino, D Sassoon, P Barton and M Buckingham (1990). Developmental regulation of myosin gene expression in mouse cardiac muscle. J Cell Biol 111:2427-2436.
35. McDonald, K S, M R Wolff and R L Moss (1998). Force-velocity and power-load curves in rat skinned cardiac myocytes. J Physiol 511:519-531.
36. Mercadier, J J, A M Lompre, C Wisnewsky, J L Samuel, J Bercovici, B Swynghedauw and K Schwartz (1981). Myosin isoenzymic changes in several models of rat cardiac hypertrophy. Circ Res 49:525-532.
37. Millar, N C and E Homsher (1990). The effect of phosphate and calcium on force generation in glycerinated rabbit skeletal muscle fibers. J Biol Chem 265: 20234-20240.
38. Miyata, S, W Minobe, M R Bristow and L A Leinwand (2000). Myosin heavy chain isoform expression in the failing and nonfailing human heart. Circ Res 86:386-390.
39. Morkin, E (1993). Regulation of myosin heavy chain genes in the heart. Circulation 87:1451-1460.
40. Moss, R L (1992). Ca2+ regulation of mechanical properties of striated muscle: mechanistic studies using extraction and replacement of regulatory proteins. Circ Res 70:865-884.
41. Moss, R L (1999). Plasticity in the dynamics of myocardial contraction—Ca2+, crossbridge kinetics or molecular cooperation. Circ Res 84:862-865.
42. Moss, R L, P J Reiser, M L Greaser and T J Eddinger (1990). Varied expression of myosin alkali light chains is associated with altered speed of contraction in rabbit fast twitch skeletal muscles. In: The Dynamic State of Muscle Fibres, edited by D. Pette. Berlin: de Gruyter, pp 355-368.
43. Nagai, R, N Pritzl, R B Low, W S Stirewalt, R Zak, N R Alpert and R Z Litten (1987). Myosin isozyme synthesis and mRNA levels in pressure-overloaded rabbit hearts. Circ Res 60:692-699.
44. Ng, W A, I L Grupp, A Subramaniam and J Robbins (1991). Cardiac myosin heavy chain mRNA expression and myocardial function in the mouse heart. Circ Res 69:1742-1750.
45. Noland, T A Jr and J F Kuo (1991). Protein kinase C phosphorylation of cardiac troponin I or troponin T inhibits Ca2+-stimulated actomyosin ATPase activity. J Biol Chem 266:4974-4978.
46. O'Gorman, S, N A Dagenais, M Qian and Y Marchuk (1997). Protamine-cre recombinase transgenes efficiently recombine target sequences in the male germ line of mice, but not in embryonic stem cells. Proc Natl Acad Sci 94:14602-14607.
47. Patel, J R, G M Diffee and R L Moss (1996). Myosin regulatory light chain modulates the Ca2+ dependence of the kinetics of tension development in skeletal muscle fibers. Biophys J 70:2333-2340.
48. Patel, J R, K S McDonald, M R Wolff and R L Moss (1997). Ca2+ binding to troponin C in skinned skeletal muscle fibers assessed with caged Ca2+ and Ca2+ fluorophore: Invariance of Ca2+ binding as a function of sarcomere length. J Biol Chem 272:6018-6027.
49. Pawloski-Dahm, C M, G Song, D L Kirkpatrick, J Palermo, J Gulick, G W Dorn, J Robbins and R A Walsh (1998). Effects of total replacement of atrial myosin light chain-2 with the ventricular isoform in atrial myocytes of transgenic mice. Circulation 97:1508-1513.
50. Rayment, I, (1996). The structural basis of the myosin ATPase activity. J Biol Chem 271:15850-15853.
51. Rayment, I, W R Rypniewski, K Schmidt-Base, R Smith, D R Tomchick, M M Benning, D A Winkelmann, G Wesenberg and H H Holden (1993). Three-dimensional structure of myosin subfragment-1: A molecular motor. Science 261:50-58.
52. Rovner, A, Y Freyzon and K Trybus (1997). An insert in the motor domain determines the functional properties of expressed smooth muscle myosin isoforms. J Muscle Res Cell Motil 18:103-110.
53. Sant'Ana Pereira, J A A, S Ennion, A J Sargeant, A F M Moorman and G Goldspink (1997). Comparison of the molecular, antigenic and ATPase determinants of fast myosin heavy chains in rat and human: a single fibre study. Eur J Physiol 435:151-163.
54. Schiaffino, S and C Reggiani (1996). Molecular diversity of myofibrillar proteins: gene regulation and functional significance. Physiol Rev 76:371-423.
55. Seidman, C E and J G Seidman (1998). Molecular genetic studies of familial hypertrophic cardiomyopathy. Basic Res Cardiol 93:Suppl 3, 13-16.
56. Siemankowski, R F, M O Wiseman and H D White. (1985). ADP dissociation from acto-S1 is sufficiently slow to limit unloaded shortening velocity in muscle. J Biol Chem 82:658-662.
57. Simnett, S J, S Libscomb, C C Ashley and I P Mulligan (1993). The effect of EMD 57033, a novel cardiotonic agent, on relaxation of skinned cardiac and skeletal muscle produced by photolysis of diazo-2, a caged calcium chelator. Pflug Archiv 425:175-177.
58. Solaro, R J and H M Rarick (1998). Troponin and tropomyosin—proteins that switch on and tune in the activity of cardiac myofilaments. Circ Res 83:471-480.
59. Spudich, J A (1994). How molecular motors work. Nature 372:515-518.
60. Strang, K T, N K Sweitzer, M L Greaser and R L Moss (1994). β-Adrenergic receptor stimulation increases unloaded shortening velocity of skinned single ventricular myocytes from rats. Circ Res 74:542-549.
61. Suguira, S, N Kobayakawa, H Fujita, H Yamishita, S Momomura, S Chaen, M Omata and H Sugi (1998). Comparison of unitary displacements and forces between two cardiac myosin isoforms by the optical trap technique. Circ Res 82:1029-1034.
62. Swartz, D R and R L Moss. (1992). Influence of a strong-binding myosin analog on calcium sensitive mechanical properties of skinned skeletal muscle fibers. J Biol Chem 267:20497-20506.
63. Sweeney, H L, M J Kushmerick, K Mabuchi, J Gergely and F A Sreter (1986). Velocity of shortening and myosin isoenzymes in two types of rabbit fast-twitch muscles. Am J Physiol 251:C431-C434.
64. Sweeney, H L, M J Kushmerick, K Mabuchi, F A Sreter and J Gergely (1988). Myosin alkali light chain and heavy chain variations correlate with altered shortening velocity of isolated skeletal muscle fibers. J Biol Chem 263:9034-9039.
65. Sweeney, H L, S S Rosenfeld, F Brown, L Faust, J Smith, J Xing, L A Stein and J R Sellers (1998). Kinetic tuning of myosin via a flexible loop adjacent to the nucleotide binding pocket. J Biol Chem 273:6262-70.
66. Sweitzer, N K and R L Moss (1993). Determinants of loaded shortening velocity in single cardiac myocytes permeabilized with α-hemolysin. Circ Res 73:1150-1162.
67. Swynghedauw, B (1986). Developmental and functional adaptations of contractile proteins in cardiac and skeletal muscles. Physiol Rev 66:710-771.
68. Uyeda, T Q, K M Ruppel and J A Spudich (1994). Enzymatic activities correlate with chimaeric substitution at the actin-binding face of myosin. Nature 368:567-569.
69. Vale, R D and R A Milligan (2000). The way things move: Looking under the hood of molecular motor proteins. Science 288:88-95.
70. VanBuren, P, D E Harris, N R Alpert and D M Warshaw (1995). Cardiac V1 and V3 myosins differ in their hydrolytic and mechanical activities in vitro. Circ Res 77:439-444.
71. VanBuren, P, G S Waller, D E Harris, K M Trybus, D M Warshaw and S Lowey (1994). The essential light chain is required for full force production by skeletal muscle myosin. Proc Natl Acad Sci 91:12403-12407.
72. Walker, J W, Z Lu and R L Moss (1992). Effects of Ca2+ on the kinetics of phosphate release in skeletal muscle. J Biol Chem 267:1-8
73. Weiner, M P, G L Costa, W Schoettlin, J Cline, E Mathur and J C Bauer (1994). Site-directed mutagenesis of double-stranded DNA by the polymerase chain reaction. Gene 151:119-123.
74. Woledge, R C, N A Curtin and E Homsher (1985). *Energetic aspects of muscle contraction*. Academic Press London, pp 45-75.
75. Wolff, M R, S H Buck, S W Stoker and R M Mentzer (1996). Myofibrillar calcium sensitivity of tension is increased in human dilated cardiomyopathies. Role of altered β-adrenergically mediated myofibrillar protein phosphorylation. J Clin Invest 98:167-176.
76. Wolska, B, R Keller, C Evans, K Palmiter, R Phillips, M Muthuchamy, J Oehlenschlager, D Wieczorek, P, deTombe and R J Solaro (1999). Correlation between myofilament response to Ca2+ and altered dynamics of contraction and relaxation in transgenic cardiac cells that express β-tropomyosin. Circ Res 84:745-51.
77. Wolska B M and R J Solaro (1996). Method for isolation of adult mouse cardiac myocytes for studies of contraction and microfluorimetry. Am J Physiol 271:H1250-1255.

What is claimed is:

1. A homozygous transgenic mouse having incorporated into its genome a transgene comprising a nucleic acid encoding a mouse cardiac alpha myosin heavy chain comprising an S342G mutation in ATPase loop 1 of the cardiac alpha myosin heavy chain, which reduces electrostatic interaction between ATPase loop 1 and interactive micro-domain of said cardiac alpha myosin heavy chain, thereby reducing an ADP dissociation rate of said mouse cardiac alpha heavy chain, wherein said mouse exhibits: (a) reduced contractility; and (b) increased power generating work capacity resulting in the transgenic mouse exhibiting a reduced heart rate.

* * * * *